US011014959B2

(12) United States Patent
Collins et al.

(10) Patent No.: US 11,014,959 B2
(45) Date of Patent: May 25, 2021

(54) SOLVENT SYSTEM FOR SOLID PHASE PEPTIDE SYNTHESIS

(71) Applicant: CEM Corporation, Matthews, NC (US)

(72) Inventors: Jonathan McKinnon Collins, Charlotte, NC (US); Sandeep K. Singh, Charlotte, NC (US)

(73) Assignee: CEM Corporation, Matthews, NC (US)

( * ) Notice: Subject to any disclaimer, the term of this patent is extended or adjusted under 35 U.S.C. 154(b) by 0 days.

(21) Appl. No.: 16/440,893

(22) Filed: Jun. 13, 2019

(65) Prior Publication Data

US 2019/0382438 A1 Dec. 19, 2019

Related U.S. Application Data

(60) Provisional application No. 62/685,052, filed on Jun. 14, 2018.

(51) Int. Cl.
*C07K 1/00* (2006.01)
*C07K 1/04* (2006.01)

(52) U.S. Cl.
CPC ....................... *C07K 1/04* (2013.01)

(58) Field of Classification Search
None
See application file for complete search history.

(56) References Cited

U.S. PATENT DOCUMENTS

| 5,830,637 A | 11/1998 | Frank et al. |
| 2010/0286359 A1 | 11/2010 | Srivastanva et al. |
| 2014/0275481 A1* | 9/2014 | Simon .................... C07K 1/042 530/335 |
| 2015/0353456 A1 | 12/2015 | Yoshimoto et al. |
| 2016/0002408 A1 | 1/2016 | Sidenstick et al. |
| 2017/0349706 A1 | 12/2017 | Ben-Asher et al. |

FOREIGN PATENT DOCUMENTS

WO 2015/128687 A1 9/2015

OTHER PUBLICATIONS

Fang-Yuan, J. Chem. Eng. Data, 2003, 48, 224-225.*
L. Varanda and M. Miranda, "Solid-phase peptide synthesis at elevated temperatures: a search for an optimized synthesis condition of unsulfated cholecystokinin-12," J. Peptide Res., vol. 50, No. 2, pp. 102-108, 1997.
Y. Jad, G. Acosta, S. Khattab, B. de la Torre, T. Govender, H. Kruger, A. El-Faham and F. Albericio, "Peptide synthesis beyond DMF:THF and ACN as excellent and friendlier alternatives," Org. Biomol. Chem., vol. 13, No. 8, pp. 2393-2398, 2015.
Y. Jad, G. Acosta, T. Govender, H. Kruger, A. El-Faham, B. de la Torre and E Albericio, "Green Solid-Phase Peptide Synthesis 2. 2-Methyltetrahydrofuran and Ethyl Acetate for Solid-Phase Peptide Synthesis under Green Conditions," ACS Sustainable Chem. Eng., vol. 4, No. 12, pp. 6809-6814, 2016.
A. Kumar, Y. Jad, A. El-Faham, B. de la Torre and A. F., "Green solid-phase peptide synthesis 4. Gamma-Valerolactone and N-formylmorpholine as green solvents for solid phase peptide synthesis," Telt. Letters, vol. 58, No. 30, pp. 2986-2988, 2017.
Y. Jad, T. Govender, K. H.G., A. El-Faham, B. de la Torre and F. Albericio, "Green Solid-Phase Peptide Synthesis (GSPPS) 3. Green Solvents for Fmoc Removal in Peptide Chemistry," Org. Process Res. Dev., vol. 21, No. 3, pp. 365-369, 2017.
S. Lawrenson, R. Arav and M. North, "The greening of peptide synthesis," Green Chem., vol. 19, p. 1685-1691, 2017.
S. Lawrenson, M. North, F. Peigneguy and A. Routledge, "Greener solvents for solid-phase synthesis," Green Chem., vol. 19, pp. 952-962, 2017.
M. Beyermann, P. Henklein, A. Klose, R. Sohr and M. Bienert, "Effect of tertiary amine on the carbodiimide-mediated peptide synthesis," Int. J. Peptide Protein Res., vol. 37, pp. 252-256, 1991.
L. Carpino and A. El-Faham, "The Diisopropylcarbodiimide/1-Hydroxy-7-azabenzotriazole System: Segment Coupling and Stepwise Peptide Assembly," Tetrahedron, vol. 55, pp. 6813-6830, 1999.
E. Atherton, N.L. Benoiton, E. Brown, R. Sheppard and B.J. Williams, "Racemisation of Activated, Urethane-protected Amino-acids by p-Dimethylaminopyridine. Significance in Solid-phase Peptide Synthesis," JCS Chem. Comm., pp. 336-337, 1981.
S. Wang, J. Tam, B. Wang and R. Merrifield, "Enhancement of peptide coupling reactions by 4-dimethylaminopyridine," Int. J. Peptide Protein Res., vol. 18, pp. 459-467, 1981.
M. Pennington and M. Byrnes, "Procedures to Improve Difficult Couplings," from: Methods in Molecular Biology, vol. 35: Peptide Synthesis Protocols, Totowa, NJ, Humana Press, 1994, p. 1.
J. Collins, K. Porter, S. Singh and G. Vanier, "High-Efficiency Solid Phase Peptide Synthesis (HE-SPPS)," Org. Lett., vol. 16, pp. 940-943, 2014.
X. Shangjie, I. Held, B. Kempf, H. Mayr, W. Steglich and H. Zipse, "The DMAP-Catalyzed Acetylation of Alcohols—A Mechanistic Study (DMAP=4(Dimethylamino)pyridine)," Chem. Eur. J. vol. 11, pp. 4751-4757, 2005.
Lopez et al., "N-Butylpyrrolidinone as Alternative Solvent for Solid-Phase Peptide Synthesis," Org. Process Res. Dev., ACS Publications, 2018, 22, pp. 494-503.
A. Tofteng, S. Pedersen, D. Staerk and K. Jensen, "Effect of Residual Water and Microwave Heating on the Half-Life of the Reagents and Reactive Intermediates in Peptide Synthesis," Chem. Eur. J., vol. 18, pp. 9024-9031, 2012.
K. Wehrstedt, P. Wandrey and D. Heitkamp, "Explosive properties of 1-hydroxybenzotriazoles," J. Hazardous Materials, vol. A126, pp. 1-7, 2005.

(Continued)

*Primary Examiner* — Jeanette M Lieb
(74) *Attorney, Agent, or Firm* — Addition, Pendleton & Witherspoon, P.A.

(57) ABSTRACT

A solvent system for solid phase peptide synthesis is disclosed that combines a morpholine-based compound and an alkoxybenzene-based compound to form a solvent that can be compatible with both polystyrene and/or PEG resins and that can produce purity yields at least comparable to conventional solvents such as DMF, DMA, and/or NMP.

51 Claims, 10 Drawing Sheets

Specification includes a Sequence Listing.

(56) References Cited

OTHER PUBLICATIONS

M. Itoh, "Peptides. IV. Racemization Suppression by the Use of Ethyl-2-Hydroximino-2-cyanoacetate and Its Amide," Bulletin Chem. Soc. Jpn., vol. 46, pp. 2219-2221, 1973.

S. Palasek, Z. Cox and J. Collins, "Limiting racemization and aspartimide formation in microwave-enhanced Fmoc solid phase peptide synthesis," J Pept. Sci., vol. 13, pp. 143-148, 2007.

J. Perich, N. Ede, S. Eagle and A. Bray, "Synthesis of phosphopeptides by the Multipin method: Evaluation of coupling methods for the incorporation of Fmoc-Tyr(PO3BzI,H)-OH, Fmoc-Ser(PO3BzI,H)-OH and Fmoc-Thr(PO3BzI,H)-OH," Lett. Pept. Sci., vol. 6, pp. 91-97, 1999.

L. Carpino and A. El-Faham, "Effect of Tertiary Bases on O-Benzotriazolyuronium Salt-Induced Peptide Segment Coupling," J. Org. Chem., vol. 59, pp. 695-698, 1994.

T. Lescrinier, R. Busson, H. Winter, C. Hendrix, G. Janssen, C. Pannecouque, J. Rozenski, A. Aerschot and P. Herdewijn, "a-Amino acids derived from ornithine as building blocks for peptide synthesis," J. Peptide Res., vol. 49, pp. 183-189, 1997.

S. Nozaki, "Delay of coupling caused by excess additives," J. Peptide Sci., vol. 12, pp. 147-153, 2006.

R. Subiros-Funosas, R. Prohens, R. Barbas, A. El-Faham and F. Albericio, "Oxyma: An Efficient Additive for Peptide Synthesis to Replace the Benzotriazole-Based HOBt and HOAt with a Lower Risk of Explosion," Chem. Eur. J., vol. 15, pp. 9394-9403, 2009.

M. Cezari and L. Juliano, "Studies on lactam formation during coupling procedures of N alpha-N omega-protected arginine derivatives," J. Pept. Res., vol. 9, pp. 88-91, 1996.

R. Subiros-Funosas et al., "Use of Oxyma as pH Modulatory Agent to be Used in the Prevention of Base-Driven Side Reactions and its Effect on 2-Chlorotrityl Chloride Resin," Pept. Sci., vol. 98, pp. 89-97, 2012.

I. Friligou, E Papadimitriou, D. Gatos, J. Matsoukas and T. Tselios, "Microwave-assisted solid-phase peptide synthesis of the 60-110 domain of human pleiotrophin on 2-chlorotrityl resin," Amino Acids, vol. 40, pp. 1431-1440, 2011.

International Search Report and Written Opinion in counterpart International Application No. PCT/US19/37092, dated Aug. 9, 2019, pp. 1-17.

P. White, J. Collins and Z. Cox, "Comparative study of conventional and microwave assisted synthesis," in 19th American Peptide Symposium, San Diego, CA, 2005, p. 1.

J. Collins, "Microwave-Enhanced Synthesis of Peptides, Proteins, and Peptidomimetics," Microwaves in Organic Synthesis, 3rd Ed., Weinheim, Germany, Wiley-VCH Verlag GmbH & Co. KGaA, 2012, pp. 897-959.

J. Pawlas et al., "2D green SPPS: green solvents for on-resin removal of acid sensitive protecting groups and lactamization," Green Chemistry, 2019, 21, pp. 2594-2600.

* cited by examiner

SEQUENCE LISTING

```
<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: Synthesized

<400> SEQUENCE: 1

Val Gln Ala Ala Ile Asp Tyr Ile Asn Gly
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthesized

<400> SEQUENCE: 2

Trp Phe Thr Thr Leu Ile Ser Thr Met
1               5

<210> SEQ ID NO 3
<211> LENGTH: 28
<212> TYPE: PRT
<213> ORGANISM: Artificial Sequence
<220> FEATURE:
<223> OTHER INFORMATION: Synthesized

<400> SEQUENCE: 3

Ser Asp Ala Ala Val Asp Thr Ser Ser Glu Ile Thr Thr Lys Asp Leu
1               5                   10                  15

Lys Glu Lys Lys Glu Val Val Glu Glu Ala Glu Asn
            20                  25

<210> SEQ ID NO 4
<211> LENGTH: 20
<212> TYPE: PRT
<213> ORGANISM: Artificial Sequence
<220> FEATURE:
<223> OTHER INFORMATION: Synthesized

<400> SEQUENCE: 4

Val Tyr Trp Thr Ser Pro Phe Met Lys Leu Ile His Glu Gln Cys Asn
1               5                   10                  15

Arg Ala Asp Gly
            20
```

SOLVENT SYSTEM FOR SOLID PHASE PEPTIDE SYNTHESIS

CROSS-REFERENCE TO PRIORITY APPLICATION

This application claims the benefit U.S. Provisional Patent Application Ser. No. 62/685,052, for Solvent System for Solid Phase Peptide Synthesis, filed Jun. 14, 2018, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Aug. 28, 2019, is titled "7100_282_sequence_listing_ST25.txt" and is 1,339 bytes in size.

BACKGROUND

Since its introduction in 1963 by Dr. Bruce Merrifield, solid phase peptide synthesis (SPPS) has been a powerful technique for the generation of synthetic peptides. Its process of stepwise assembly of a peptide on a solid resin allows for drastic simplification of isolation and washing between each reaction step. The use of this technology has allowed for the synthesis even at a large scale of fairly long and complex peptides.

The dominant chemistry utilized in SPPS is based on the Fmoc protecting group with orthogonal acid labile side chain protecting groups (Trityl, t-butyl, Pbf, etc.).

Standard resins are composed of polystyrene and to a lesser extent polyethyleneglycol (PEG) units.

In the last two decades, SPPS has been enhanced with the development of microwave based systems and other technologies to increase temperature. These technologies allow for improved reaction rates and improved washing at higher temperatures.

The primary solvents used in SPPS are dimethylformamide (DMF), dimethylacetamide (DMA), and N-methylpyrrolidinone (NMP). Their use extends from the ability to effective dissolve the Fmoc amino acids and other starting reagents, properly swell the resins used, minimize aggregation of the growing peptide chain during assembly, and effectively wash the resin clean between synthesis steps. Each of these characteristics is essential to properly assemble a peptide in good quality. This is inherent in the fact that the process requires many iterative steps which must all proceed efficiently.

Additionally, a good solvent for SPPS must also have certain physical properties. These include a low viscosity and relatively high boiling point (>100° C.). A low viscosity is required because SPPS is largely automated and requires many filtration steps. At higher viscosities, flow rates and draining can be insufficient leading to synthesis interruptions and engineering challenges. A higher boiling point is required to make the system compatible with elevated temperature approaches where reaction conditions are routinely heated to 90-100° C.

Traditional SPPS solvents (e.g., DMF, DMA, NMP) have been classified as reprotoxic by the REACH chemical legislation in Europe. DMF, DMA, NMP have thus being placed on the Candidates of High Concern List, thereby increasing the need for alternative solvents.

To date, there have been numerous attempts to develop an alternative solvent for SPPS. Some of these efforts have been focused on developing new protecting group strategies and/or resins that would work well in alternative solvents, such as water. However, the global supply of Fmoc amino acids and polystyrene resins have been extensively developed with good supply, quality and low cost. Therefore, a solvent system that is compatible with Fmoc amino acids and polystyrene resins would have significant advantages.

Alterative solvents have been explored while still using Fmoc derivatives and standard resins (polystyrene and PEG). A mixture of toluene and Dimethyl sulfoxide (DMSO) was disclosed in an Fmoc SPPS process at elevated temperature. L. Varanda and M. Miranda, *J Pept. Res.*, vol. 50, no. 2, pp. 102-108, 1997. However, the results obtained with this study indicated low purity. Additionally, toluene is a less desirable solvent due to its toxicity and classification as a potential reprotoxin.

The use of tetrahydrofuran (THF) and Acetonitrile (ACN) have similarly been disclosed as more environmentally friendly solvents for SPPS. Y. Jad, G. Acosta, S. Khattab, B. de la Torre, T. Govender, H. Kruger, A. El-Faham and F. Albericio, *Org. Biomol. Chem.*, vol. 13, no. 8, pp. 2393-2398, 2015. However, both of these solvents have boiling points under 100° C. and some toxicity issues.

As a proposed improvement, 2-methyltetrahydrofuran (2-Me-THF) as a solvent in combination with ethyl acetate (EtOAc) washing steps for an SPPS process was later published. Y. Jad, G. Acosta, T. Govender, H. Kruger, A. El-Faham, B. de la Torre and F. Albericio, *ACS Sustainable Chem. Eng.*, vol. 4, no. 12, pp. 6809-6814, 2016. 2-Me-THF, however, is still limited by a lower boiling point (80° C.) and was found to be unsuitable for polystyrene resins. Additionally, even when PEG based resins such as ChemMatrix were used and elevated temperature, purity lower than when using DMF was obtained.

More recently, additional solvents for SPPS were considered including γ-valerolactone and N-formylmorpholine (NFM). A. Kumar, Y. Jad, A. El-Faham, B. de la Torre and A. F., *Tett. Letters*, vol. 58, no. 30, pp. 2986-2988, 2017; Y. Jad, T. Govender, K. H. G., A. El-Faham, B. de la Torre and F. Albericio, *Org. Process Res. Dev.*, vol. 21, no. 3, pp. 365-369, 2017. Both γ-valerolactone and NFM display low toxicity in animal studies while also having high boiling points making them attractive replacement solvents for SPPS. These solvents were found to synthesize a difficult peptide on a polystyrene resin in better purity than when using 2-Me-THF, but still at substantially lower purity than with DMF. Both γ-valerolactone and NFM are unable to dissolve Fmoc amino acids at 0.2M concentration, which is significantly lower than in DMF. Also, NFM has the additional undesirable property that its melting point (20-23° C.) is near room temperature and is thus difficult to work with due to its extremely high viscosity and potential to solidify. Thus, in slightly cooler environments it will require a warming step prior to use as a solvent. For these reasons, the authors recommend γ-valerolactone as the preferred choice.

In a separate report, the use of propylene carbonate has been explored as a green solvent for SPPS. S. Lawrenson, R. Arav and N. M., *Green Chem.*, vol. 19, p. 1685, 2017. However, propylene carbonate does not adequately swell polystyrene resins thereby requiring the use of a PEG based resin. S. Lawrenson, M. North, F. Peigneguy and A. Routledge, *Green Chem.*, vol. 19, pp. 952-962, 2017. Additionally, Fmoc amino acids displayed low solubility in propylene carbonate thereby requiring pre-mixing with an activating solution for dissolution.

It was found to provide similar results to DMF in certain cases and have preferable properties such as low toxicity and a high boiling point and flash point. However, this solvent contains an ester moiety thereby making it potentially reactive at particularly at higher temperatures. Additionally, the solubility of Fmoc amino acids appears less in γ-valerolactone than compared to DMF.

Common solvents are rated in the following table.

| ACS Solvent Selection Guide (1 = best, 10 = worst) | | | | | |
|---|---|---|---|---|---|
| | Use | | Environment | | |
| | Safety | Health | Air | Water | Waste |
| Solvent | | | | | |
| Acetonitrile | 3 | 5 | 6 | 4 | 6 |
| Anisole | 5 | 4 | | 3 | 4 |
| DCM | 2 | 7 | 9 | 6 | 7 |
| DMA | 2 | 7 | 3 | 7 | 7 |
| DMF | 3 | 7 | 3 | 2 | 7 |
| DMSO | 3 | 4 | 4 | 4 | 8 |
| Ethyl Acetate | 5 | 4 | 6 | 4 | 4 |
| NMP | 3 | 6 | 6 | 2 | 7 |
| Propylene Carbonate | | | | | |
| 2-Me-THF | 5 | 6 | | | 4 |
| THF | 5 | 6 | 5 | 4 | 5 |
| Toluene | 5 | 7 | 6 | 6 | 2 |

SUMMARY

The present disclosure relates to a solvent system for solid phase peptide synthesis (SPPS). In exemplary embodiments, the solvent system includes a solvent mixture including a morpholine-based compound, for example, N-formylmorpholine (also referred to herein as NFM), and an alkoxybenzene-based compound. For example, the solvent mixture can include N-formylmorpholine and 1,3-dimethoxybenzene. As another example, the solvent mixture can include N-formylmorpholine and an anisole-based compound. In other exemplary embodiments, the solvent mixture can include N-butylpyrrolidinone (also referred to herein as NBP) and an alkoxybenzene-based compound, such as 1,3-dimethoxybenzene and/or an anisole-based compound.

The present disclosure also relates to a solid phase peptide synthesis (SPPS) method. In exemplary embodiments, the SPPS method includes the steps of; deprotecting a first amino acid linked to a solid phase resin by removing a protective chemical group to form a deprotected amino acid; washing the deprotected amino acid; coupling a second amino acid to the deprotected amino acid to form a peptide from the first and second amino acids; and repeating the deprotecting, washing, and coupling steps to form a peptide comprising the first, second, and successive amino acids. In the method, the deprotecting, washing, and/or coupling steps are performed in the presence of a solvent system comprising a solvent mixture including a morpholine-based compound, for example N-formylmorpholine, and an alkoxybenzene-based compound. In other exemplary embodiments of the method, the deprotecting, washing, and/or coupling steps are performed in the presence of a solvent system comprising a solvent mixture including NBP and an alkoxybenzene-based compound.

The present disclosure also relates to a composition for solid phase peptide synthesis (SPPS) comprising an amino acid linked to a solid phase resin; and a solvent system for solid phase peptide synthesis (SPPS) comprising a solvent mixture including a morpholine-based compound, for example N-formylmorpholine, and an alkoxybenzene-based compound. Other exemplary embodiments relate to a composition for solid phase peptide synthesis (SPPS) comprising an amino acid linked to a solid phase resin; and a solvent system for solid phase peptide synthesis (SPPS) comprising a solvent mixture including NBP and an alkoxybenzene-based compound.

The present disclosure also relates to a composition comprising a peptide chain linked to a solid phase resin; and a solvent system for solid phase peptide synthesis (SPPS) comprising a solvent mixture including a morpholine-based compound, for example N-formylmorpholine, and an alkoxybenzene-based compound. Other exemplary embodiments relate to a composition comprising a peptide chain linked to a solid phase resin; and a solvent system for solid phase peptide synthesis (SPPS) comprising a solvent mixture including NBP and an alkoxybenzene-based compound.

The present disclosure also relates to a solid phase peptide synthesis method performed at elevated temperatures greater than 30° C. utilizing a solvent mixture of a morpholine-based compound, such as N-formylmorpholine, and an alkoxybenzene-based compound, such as a dimethoxybenzene compound and/or an anisole compound, and/or utilizing a solvent mixture of NBP and an alkoxybenzene-based compound, such as a dimethoxybenzene compound and/or an anisole compound, with a suitable viscosity for SPPS, that is compatible with both polystyrene and PEG resins, and that produces purity yields at least comparable to conventional solvents selected from the group consisting of DMF, DMA, and NMP.

The present disclosure also relates to a method of performing a solid phase peptide synthesis reaction at elevated temperatures comprising combining a morpholine-based compound, such as N-formylmorpholine, and an alkoxybenzene-based compound, such as a dimethoxybenzene compound and/or an anisole compound, and/or combining NBP and an alkoxybenzene-based compound, such as a dimethoxybenzene compound and/or an anisole compound, to form a solvent suitable for deprotection, coupling, and washing steps.

The present disclosure also relates to a solvent system for solid phase peptide synthesis at elevated temperatures comprising a combination of a morpholine-based compound, such as N-formylmorpholine, and an alkoxybenzene-based compound, such as a dimethoxybenzene compound and/or an anisole compound, and/or a solvent system for solid phase peptide synthesis at elevated temperatures comprising a combination of NBP and an alkoxybenzene-based compound, such as a dimethoxybenzene compound and/or an anisole compound, wherein the solvent system has a suitable viscosity for solid phase peptide synthesis, the solvent system is compatible with both polystyrene and PEG resins, and the solvent system can produce purity yields at least comparable to conventional solvents selected from the group consisting of DMF, DMA, and NMP.

DETAILED DESCRIPTION

Figure 1:
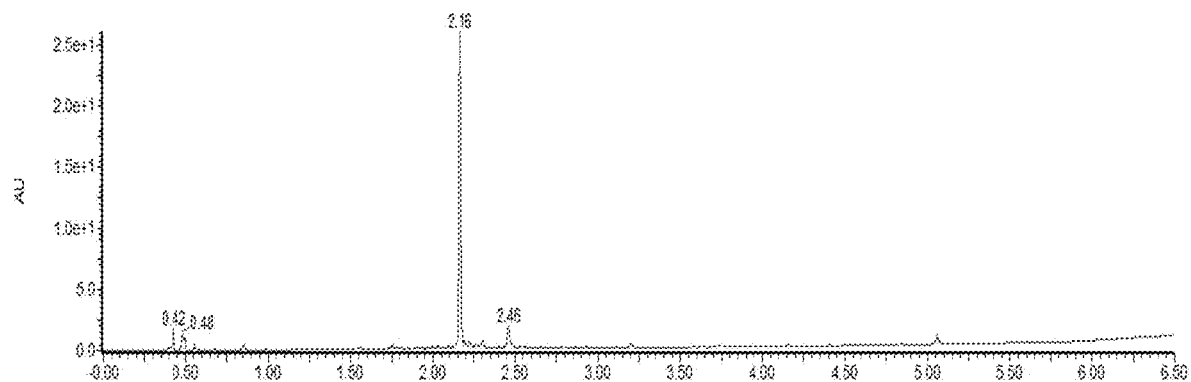
FIG. 1 is a high performance liquid chromatograph of SPPS synthesis of $^{65-74}$ ACP using DMF as the solvent and a Rink Amide ProTide resin, as described in Entry 1 in Table 1.
Figure 2:
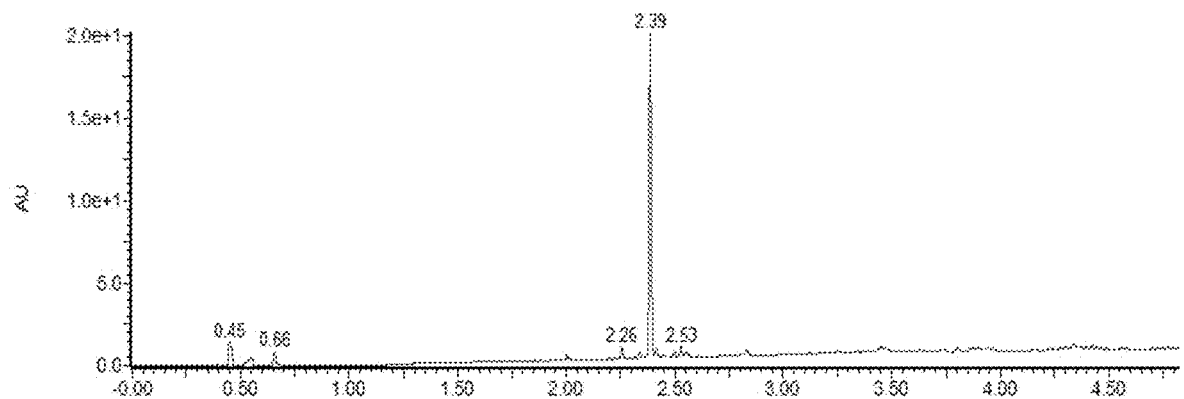
FIG. 2 is a high performance liquid chromatograph of SPPS synthesis of [65-74] ACP with 35% NFM/Anisole as the solvent and a Rink Amide ProTide resin, as described in the Entry 2 in Table 1.
Figure 3:
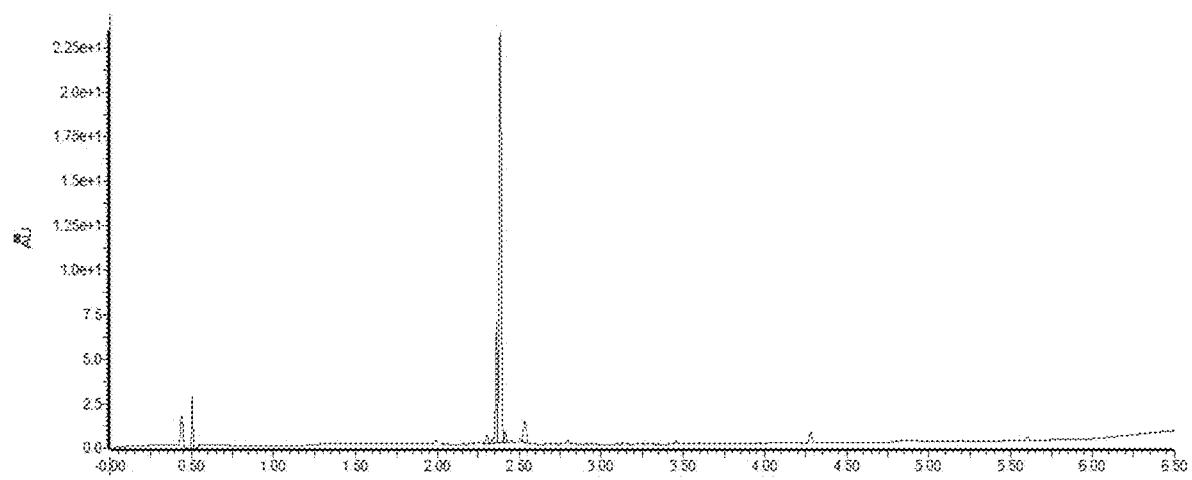
FIG. 3 is a high performance liquid chromatograph of SPPS synthesis of [65-74] ACP with 25% NFM/1,2-dimethoxybenzene (1,2-DMB) as the solvent and a Rink Amide MBHA PS resin, as described in the Entry 3 in Table 1.
Figure 4:
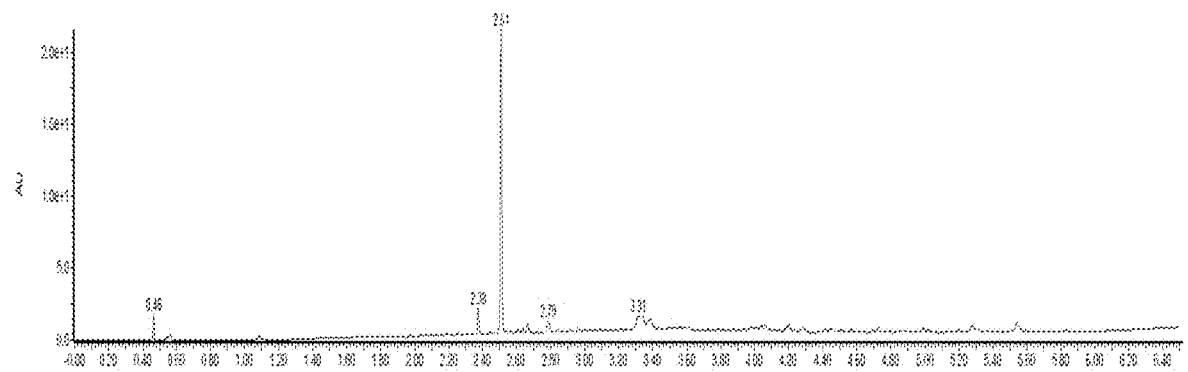
FIG. 4 is a high performance liquid chromatograph of SPPS synthesis of [65-74] ACP with 25% NFM/1,3-dimethoxybenzene (1,3-DMB) as the solvent and a Rink Amide MBHA PS resin, as described in the Entry 4 in Table 1.
Figure 5:
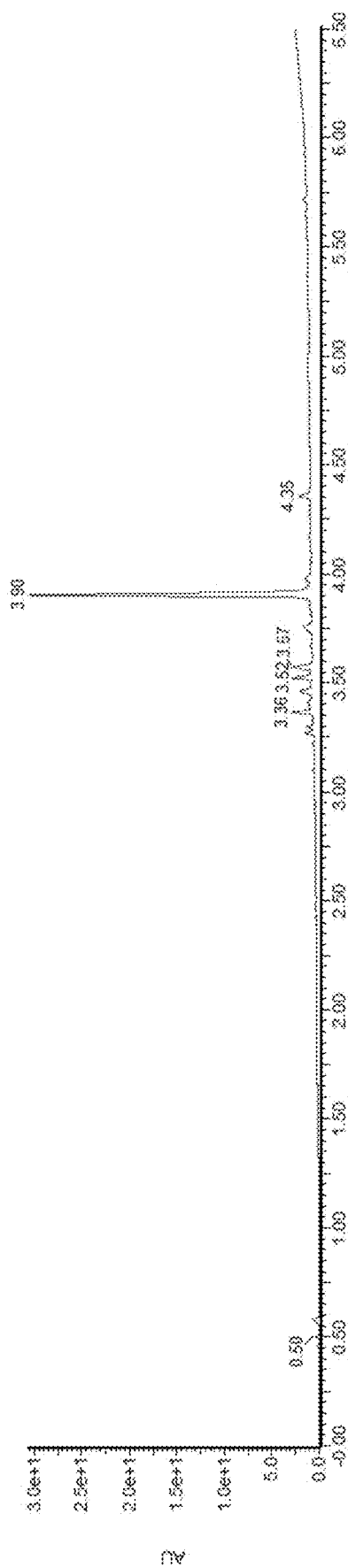
FIG. 5 is a high performance liquid chromatograph of SPPS synthesis of JR 10 mer with DMF as the solvent and a Rink Amide ProTide resin, as described in the Entry 1 in Table 2.
Figure 6:
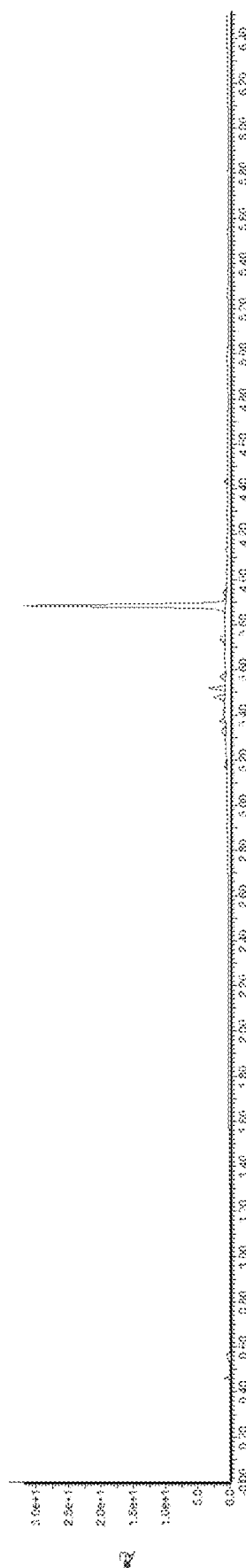
FIG. 6 is a high performance liquid chromatograph of SPPS synthesis of JR 10 mer with 25% NFM/1,3-dimethoxybenzene (1,3-DMB) as the solvent and a Rink Amide ProTide resin, as described in the Entry 2 in Table 2.
Figure 7:
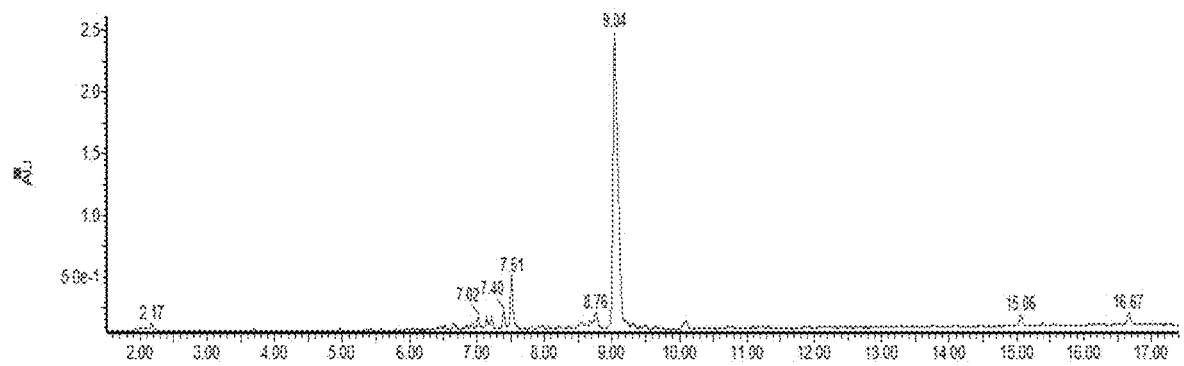
FIG. 7 is a high performance liquid chromatograph of SPPS synthesis of Thymosin with DMF as the solvent and a Rink Amide MBHA PS resin, as described in the Entry 1 in Table 3.
Figure 8:
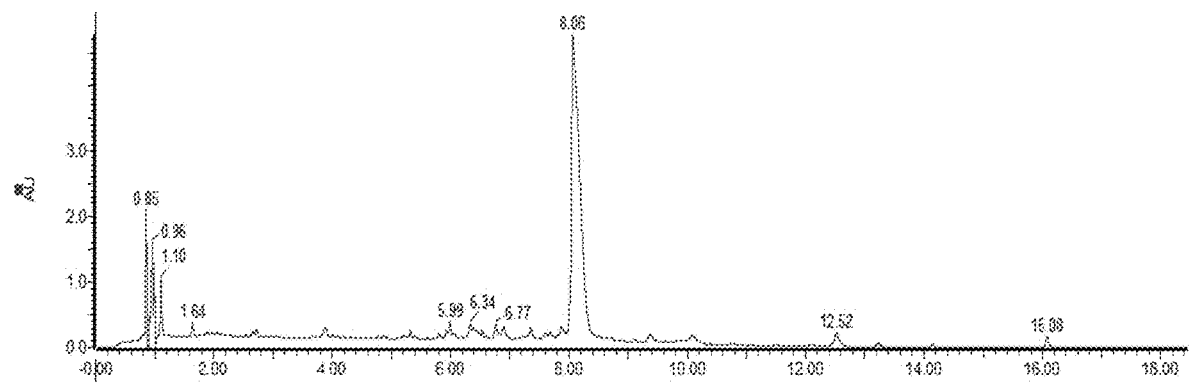
FIG. 8 is a high performance liquid chromatograph of SPPS synthesis of Thymosin with 25% NFM/Anisole as the solvent and a Rink Amide MBHA PS resin, as described in the Entry 2 in Table 3.
Figure 9:
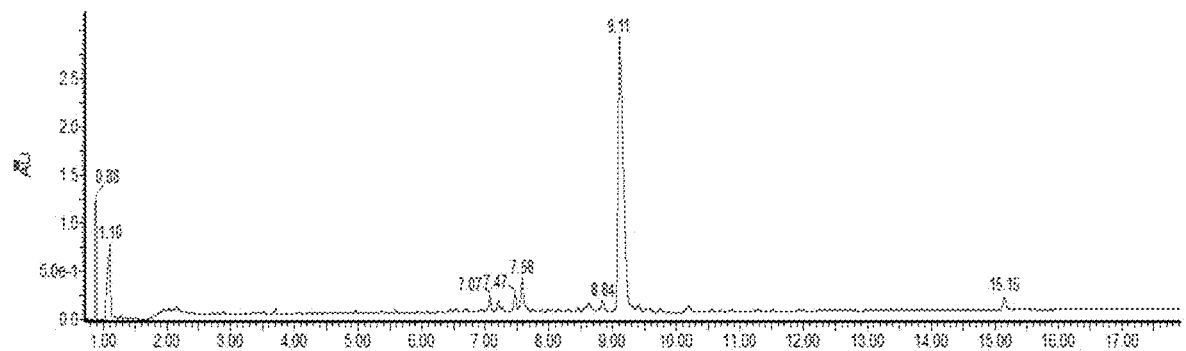
FIG. 9 is a high performance liquid chromatograph of SPPS synthesis of Thymosin with DMF as the solvent and a Rink Amide ProTide resin, as described in the Entry 3 in Table 3.
Figure 10:
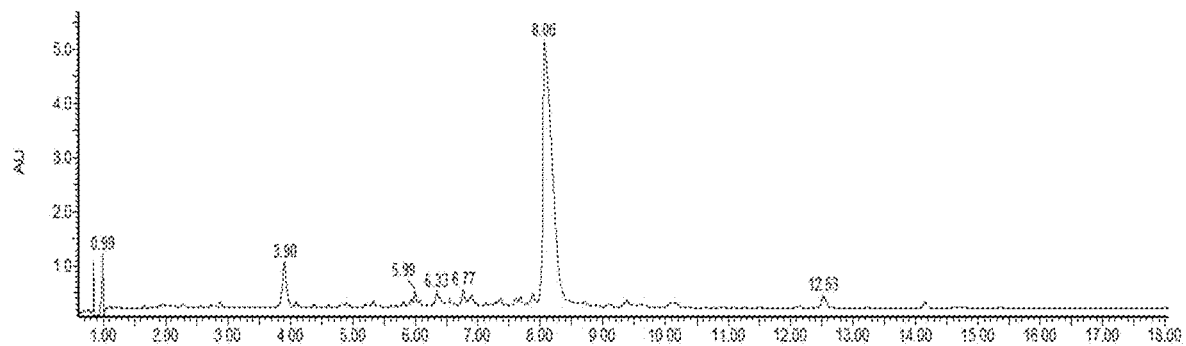
FIG. 10 is a high performance liquid chromatograph of SPPS synthesis of Thymosin with 25% NFM/Anisole as the solvent and a Rink Amide ProTide resin, as described in the Entry 4 in Table 3.
Figure 11:
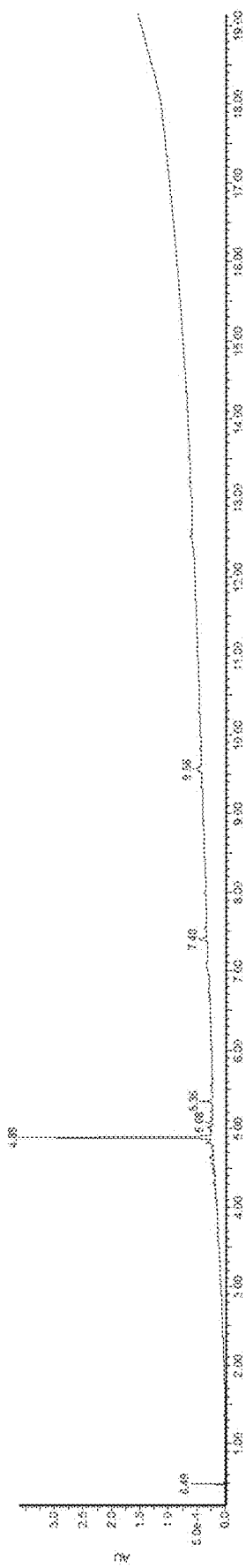
FIG. 11 is a high performance liquid chromatograph of SPPS synthesis of Thymosin with 25% NFM/1,3-dimethoxybenzene (1,3-DMB) as the solvent and a Rink Amide ProTide resin, as described in the Entry 5 in Table 3.
Figure 12:
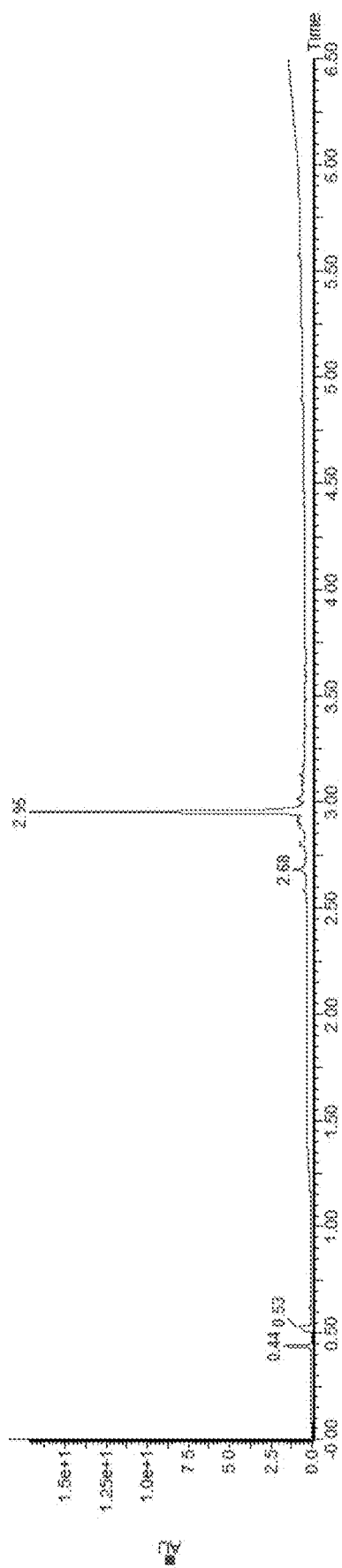
FIG. 12 is a high performance liquid chromatograph of SPPS synthesis of ABC-20 mer with DMF as the solvent and a Rink Amide ProTide resin, as described in the Entry 1 in Table 4.
Figure 13:
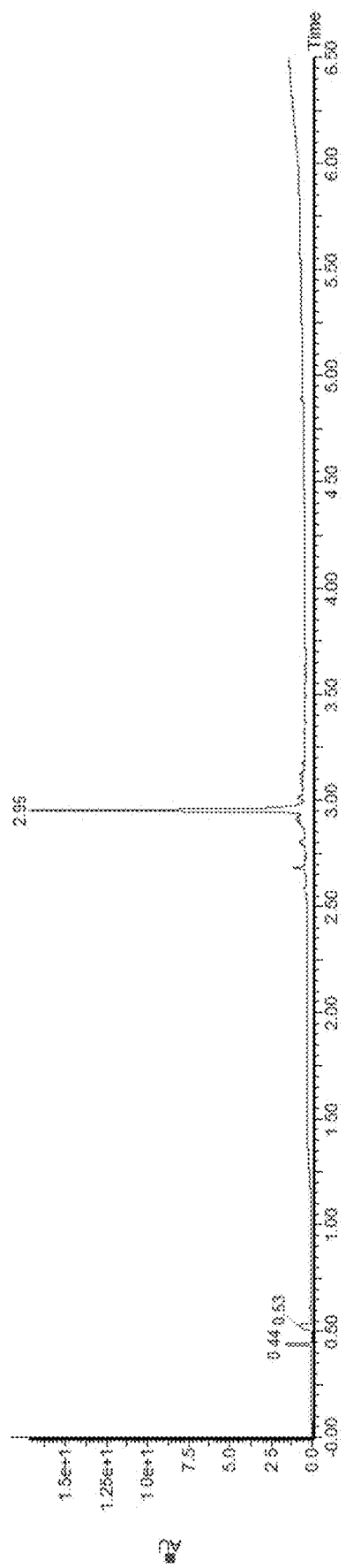
FIG. 13 is a high performance liquid chromatograph of SPPS synthesis of ABC-20 mer with 25% NFM/Anisole as the solvent and a Rink Amide ProTide resin, as described in the Entry 2 in Table 4.
Figure 14:
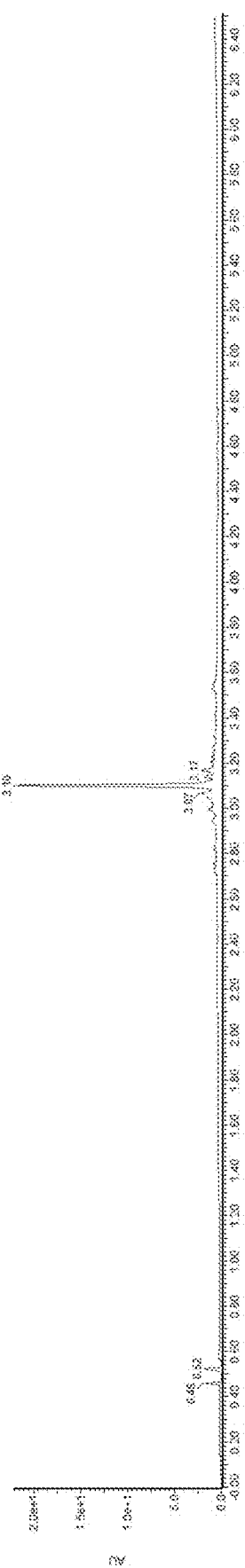
FIG. 14 is a high performance liquid chromatograph of SPPS synthesis of ABC-20 mer with 25% NFM/1,3-dimethoxybenzene (1,3-DMB) as the solvent and a Rink Amide ProTide resin, as described in the Entry 3 in Table 4.

The above and other aspects, features, and advantages of the present invention will become apparent from the detailed description of the following embodiments. It should be understood that the present invention is not limited to the following embodiments and may be embodied in different ways by those skilled in the art without departing from the scope of the present invention. Rather, the embodiments are provided for complete disclosure and to provide thorough understanding of the present invention by those skilled in the art. The scope of the present invention should be defined only by the appended claims.

The present disclosure relates to a solvent system for solid phase peptide synthesis (SPPS). In exemplary embodiments, the solvent system includes a solvent mixture including a morpholine-based compound, for example N-formylmorpholine (NFM), and an alkoxybenzene-based compound. In other exemplary embodiments, the solvent system includes a solvent mixture including N-butylpyrrolidinone (NBP) and an alkoxybenzene-based compound.

For example, the solvent mixture can include N-formylmorpholine and 1,3-dimethoxybenzene. As another example, the solvent mixture can include N-formylmorpholine and an anisole-based compound.

In other exemplary embodiments, the solvent mixture can include N-butylpyrrolidinone (also referred to herein as NBP) and 1,3-dimethoxybenzene and/or an anisole-based compound.

The solvent system can exhibit unique properties and can replace traditional SPPS solvents, such as DMF, DMA, and/or NMP. The solvent system can be compatible with polystyrene and/or PEG based resins. The solvent system can be used for steps in SPPS (such as deprotection, coupling, and/or washing, individually or in combination) with polystyrene and/or PEG based resins. The solvent system can also be used in methods using microwave energy. Further, the solvent system can effectively dissolve standard Fmoc amino acids, for example at concentrations ≥0.2M, without limitation.

In addition, the solvent system can have a low viscosity suitable for use in SPPS methods. For example, the solvent system and/or solvent mixture can have a viscosity that is less than the viscosity of NFM and/or NBP alone and can be suitable for use in automated processes such as those associated with SPPS.

The solvent systems can also be less toxic (for example, can be classified as non-reprotoxic according to relevant government regulations) and/or can be green (more environmentally friendly) than traditional SPPS solvents such as DMF, DMA, and/or NMP.

The SPPS solvent system can be used at elevated SPPS temperatures, including elevated temperatures associated with the use of microwave energy in SPPS. For example, the SPPS solvent system can be used at a temperature of about 30° C. or greater, for example about 30° C. to about 120° C., for example about 40° C. to about 120° C., for example about 70° C. to about 120° C., for example about 70° C. to about 110° C., for example about 90° C. to about 120° C., and for example about 90° C. to about 110° C., without limitation.

The solvent mixture has properties such as boiling point so that the solvent mixture is suitable for use at elevated SPPS temperatures described herein, for example, at temperatures of about 30° C. or greater, for example about 30° C. to about 120° C., for example about 40° C. to about 120° C., for example about 70° C. to about 120° C., for example about 70° C. to about 110° C., for example about 90° C. to about 120° C., and for example about 90° C. to about 110° C., without limitation.

For example, the solvent mixture can have a boiling point that is about the same as and/or greater than about the reaction temperature of one or more of SPPS reaction steps. As a non-limiting example, higher temperatures can be associated with carbodiimide based activation chemistry, for example from about 70° C. to about 110° C. Thus, in exemplary embodiments, the solvent mixture can have a boiling point higher than this range. In other exemplary embodiments, the solvent mixture can have a boiling point greater than about 100° C., for example greater than about 105° C., and as another example greater than about 110° C., or higher.

In exemplary embodiments, the solvent mixture can have a boiling point of at least about 140° C. or greater, for example a boiling point of at least about 150° C. or greater. The solvent mixture can have a boiling point up to about 250° C. or higher, for example up to about 300° C., although the present disclosure is not limited thereto.

Also in exemplary embodiments, at least one solvent of the solvent mixture, and in some embodiments each solvent of the solvent mixture, can have a boiling point of at least about 140° C. or greater, for example a boiling point of at least about 150° C. or greater. At least one solvent of the solvent mixture, and in some embodiments each solvent of the solvent mixture, can have a boiling point up to about 250° C. or higher, for example up to about 300° C., although the present disclosure is not limited thereof.

The solvent mixture can be at least as effective as traditional solvents, such as DMF, DMA, and/or NMP. As a non-limiting example, the solvent mixture of the present disclosure can produce purity yields comparable to and/or better than yields for traditional SPPS solvents, such as DMF, DMA, and/or NMP. The solvent mixture of the present disclosure can generally provide purity yields of about 70% or higher, for example, about 75% or higher, about 80% or higher, about 85% or higher, and/or about 90% or higher, without limitation. The skilled artisan will appreciate that purity yields can vary depending on conditions, reagents, resins, peptide sequence, etc. used in a SPPS method and the purity yield of a given SPPS method can be determined using techniques well known in the art.

In exemplary embodiments, the solvent mixture can have a sufficiently high flash point (the lowest temperature at which vapors of a volatile material will ignite when given an ignition source), for example for compliance with government shipping and/or storage, and other, regulations. In non-limiting examples, the solvent mixture can have a flash point of about 93° C. or higher. Flash point can be determined using known test methods, for example, in accordance with ASTM D93, *Standard Test Methods for Flash Point by Pensky-Martens Closed Cup Tester* (2013).

Without being bound by any theory or explanation, it is believed that the alkoxybenzene-based compounds can provide various benefits in the solvent systems. For example, the alkoxybenzene-based compounds can be compatible with polystyrene based resins and thus can provide good solubility of polystyrene based resins and adequately swell polystyrene based resins, which can help increase the accessibility and availability of reaction sites. The alkoxybenzene-based compounds can also be compatible with nonpolar protecting groups (such as trityl, benzyl-based protecting groups) and thus can provide good solubility of the same. The alkoxybenzene-based compounds also can be relatively inert and nonreactive even at elevated SPPS temperatures. The alkoxybenzene-based compounds also can have relatively high boiling points, for example about 140° C. and higher, and as another example about 150° C. and higher, and thus can be useful with SPPS elevated temperatures, for example reaction temperatures of about 70° C. to about 110° C., without limitation. In addition, alkoxybenzene-based compounds can have a relatively lower viscosity as compared to for example to NFM and/or NBP alone and can be suitable for use in automated processes such as those associated with SPPS. As a non-limiting example, anisole has low toxicity and low viscosity (about 0.99 mPa·s at 20° C.). Also anisole can be relatively inexpensive, thereby providing cost benefits.

In contrast, at elevated temperature SPPS the risk of side reactions is increased and the presence of an ester based solvent such as ethyl acetate is not ideal because the ester can react with the terminal amine on the growing peptide chain. For example, the terminal amine reacts with activated amino acids in solutions (activated as esters). Also solvents with relatively low boiling points (such as ethyl acetate with a boiling point of about 77° C.) are unsuitable for SPPS at elevated temperatures.

The solvent mixture can include the morpholine-based compound, for example NFM, in an amount of about 20 wt % to about 50 wt %, for example, about 25 wt % to about 50 wt %, based on 100 wt % of the solvent mixture including the morpholine-based compound such as N-formylmorpholine and the alkoxybenzene-based compound. In some embodiments, the solvent mixture can include the morpholine-based compound, for example NFM, in an amount of about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt % based on 100 wt % of the solvent mixture. Further, according to some embodiments, the morpholine-based compound, for example NFM, can be present in an amount of from about any of the foregoing amounts to about any other of the foregoing amounts.

The solvent mixture can include the alkoxybenzene-based compound in an amount of about 50 wt % to about 80 wt %, for example, about 50 wt % to about 75 wt %, based on 100 wt % of the solvent mixture including the morpholine-based compound, for example NFM, and the alkoxybenzene-based compound. In some embodiments, the solvent mixture can include the alkoxybenzene-based compound in an amount of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 wt % based on 100 wt % of the solvent mixture. Further, according to some embodiments, the alkoxybenzene-based compound can be present in an amount of from about any of the foregoing amounts to about any other of the foregoing amounts.

In other exemplary embodiments, the solvent mixture can include N-butylpyrrolidinone (NBP) in an amount of about 20 wt % to about 50 wt %, for example, about 25 wt % to about 50 wt %, based on 100 wt % of the solvent mixture including NBP and the alkoxybenzene-based compound. In some embodiments, the solvent mixture can include NBP in an amount of about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt % based on 100 wt % of the solvent mixture. Further, according to some embodiments, NBP can be present in an amount of from about any of the foregoing amounts to about any other of the foregoing amounts.

In other exemplary embodiments, the solvent mixture can include the alkoxybenzene-based compound in an amount of about 50 wt % to about 80 wt %, for example, about 50 wt % to about 75 wt %, based on 100 wt % of the solvent mixture including NBP and the alkoxybenzene-based compound. In some embodiments, the solvent mixture can include the alkoxybenzene-based compound in an amount of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 wt % based on 100 wt % of the solvent mixture. Further, according to some embodiments, the alkoxybenzene-based compound can be present in an amount of from about any of the foregoing amounts to about any other of the foregoing amounts.

The alkoxybenzene-based compound can include a compound of Formula 1:

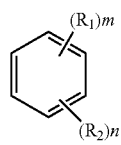

wherein:
each $R_1$ is independently —OR, wherein R is $C_1$-$C_4$ alkyl;
each $R_2$ is independently hydrogen or $C_1$-$C_4$ alkyl;
m is 1 or 2;
n is 4 or 5; and
m+n is 6.

Alkoxybenzene-based compounds of Formula 1 are known in the art and are commercially available and/or can be produced by the skilled artisan without undue experimentation.

In exemplary embodiments, the alkoxybenzene-based compound of Formula 1 can be a dialkoxybenzene-based compound, wherein m is 2. In such embodiments, each of the alkoxy substituents $R_1$ can be the same or different. For example, each $R_1$ can independently be methoxy, ethoxy, propoxy and/or butoxy, for example, each R can be methyl. Also when m is 2, in exemplary embodiments, each $R_2$ can be hydrogen. In alternative embodiments when m is 2, one or more, for example, one, two, three, or four $R_2$ can be $C_1$-$C_4$ alkyl, such as methyl, ethyl, propyl and/or butyl, and any remaining $R_2$ can be hydrogen.

An exemplary dialkoxybenzene-based compound includes 1,3-dimethoxybenzene of the following formula:

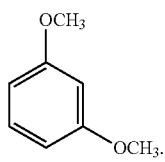

The present inventors have found that a solvent mixture including NFM and 1,3-dimethoxybenzene can have a flash point of about 93° C. or higher, and thus can be advantageous for applications requiring a minimum flash point, for example, of about 93° C. or higher.

In exemplary embodiments, the solvent mixture can include about 20 wt % to about 50 wt % NFM and about 50 wt % to about 80 wt % 1,3-dimethoxybenzene, for example about 25 wt % to about 50 wt % NFM and about 50 wt % to about 75 wt % 1,3-dimethoxybenzene, and as another example about 25 wt % NFM and about 75 wt % 1,3-dimethoxybenzene, without being limited thereto.

In other exemplary embodiments, the alkoxybenzene-based compound of Formula 1 can be an alkoxybenzene-based compound wherein m is 1. In such embodiments, the alkoxy substituent $R_1$ can be, for example, methoxy, ethoxy, propoxy or butoxy, for example R can be methyl. Also when m is 1, in exemplary embodiments, each $R_2$ can be hydrogen. In alternative embodiments when m is 1, one or more, for example, one, two, three, four, or five $R_2$ can be $C_1$-$C_4$ alkyl, such as methyl, ethyl, propyl and/or butyl, and any remaining $R_2$ can be hydrogen.

Exemplary alkoxybenzene-based compounds include anisole-based compounds. A non-limiting example of the alkoxybenzene-based compound is an anisole compound represented by the following Formula 2:

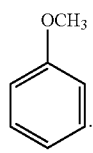

As another non-limiting example, the alkoxybenzene-based compound can be an anisole compound wherein one $R_2$ is $C_1$-$C_4$ alkyl, for example methyl, and the remaining $R_2$ are hydrogen, and wherein alkyl substituent $R_2$ is positioned ortho, meta, or para to the alkoxy substituent $R_1$. A non-limiting example of an alkyl-substituted anisole compound is represented by the following Formula 3:

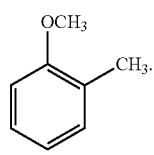

The present disclosure also relates to a solid phase peptide synthesis (SPPS) method. The skilled artisan will understand how to conduct solid phase peptide synthesis. The basics of solid phase peptide chemistry have been well-established starting with the pioneering work of Merrifield. (R. B. Merrifield (1963) "Solid Phase Peptide Synthesis I, The Synthesis of a Tetrapeptide," J. Am. Chem. Soc. 85 (14), 2149-2154). The frequently used Fmoc (9-fluorenylmethyl-oxycarbonyl) protecting-group approach is also well described in references that are easily available to the skilled person (e.g., Chan and White, "Fmoc solid phase peptide synthesis, a practical approach, Oxford University Press (2000)). Accordingly, a detailed discussion of SPPS methods is not provided.

The LIBERTY BLUE™ instrument referred to in the experiments is available from CEM Corporation of Matthews N.C. Relevant US patents dealing with the subject of solid phase peptide synthesis at elevated temperatures and using microwave irradiation include, but are not necessarily limited to, the following: U.S. Pat. Nos. 7,393,920; 7,550,560; 7,563,865; 7,939,628; 7,902,488; 7,582,728; 8,153,761; 8,058,393; 8,426,560; 8,846,862; 9,211,522. The contents of these are incorporated entirely herein by reference.

The skilled artisan will also understand the meaning of the term "amino acid" used herein in its broadest sense to refer to organic compounds that contain both amine and carboxylic acid functional groups usually along with a side chain. The skilled artisan will also appreciate that amino acids include natural amino acids (proteinogenic amino acids) and/or non-proteinogenic amino acids, and will also understand the single letter designations used to identify the same. The skilled artisan will also understand how link an amino acid to a solid phase resin and also how to join or couple amino acids to form a chain, such as short polymer chains (typically referred to in the art as peptides) and/or longer chains (typically referred to in the art as polypeptides or proteins). Accordingly, a detailed discussion of amino acids and methods known in the art for linking the same to a solid phase resin and/or for joining amino acids to form a chain is not provided. The terms peptide, polypeptide, and protein are also terms of art, the meaning of which is also understood by the skilled artisan.

As known in the art, a SPPS method can include the steps of deprotecting functional group(s) of an amino acid, coupling amino acid(s), and/or washing, for example washing after deprotecting and/or coupling steps. In the present disclosure, the method can use the solvent system including a mixture of a morpholine-based compound such as NFM and an alkoxybenzene-based compound described herein in any and/or all of deprotecting, coupling and/or washing steps (i.e., individually or in combination) of SPPS. In other exemplary embodiments of the present disclosure, the method can use the solvent system including a mixture of NBP and an alkoxybenzene-based compound described herein in any and/or all of deprotecting, coupling and/or washing steps (i.e., individually or in combination) of SPPS.

In exemplary embodiments, the SPPS method can include the following steps: deprotecting a first amino acid linked to a solid phase resin by removing a protective chemical group to form a deprotected amino acid; optionally washing the deprotected amino acid; coupling a second amino acid to the deprotected amino acid to form a peptide from the first and second amino acids; and repeating the deprotecting, washing, and coupling steps to form a peptide comprising the first, second, and successive plurality of amino acids, wherein the deprotecting, washing, and/or coupling steps are performed in the presence of a solvent system as described herein comprising a mixture including a morpholine-based compound, such as N-formylmorpholine, and an alkoxybenzene-based compound and/or comprising a mixture including NBP and an alkoxybenzene-based compound.

The SPPS method can further include, prior to coupling, activating chemical group(s) on the second amino acid (and successive amino acid(s)) using methods and agents known in the art to prepare the second (and successive) amino acid(s) for coupling with the first (and sequential) amino acid(s).

For example, the SPPS method can include the step of deprotecting in the presence of the solvent system comprising the mixture including the morpholine-based compound, such as N-formylmorpholine, and the alkoxybenzene-based compound.

As another example, the SPPS method can include the step of washing in the presence of the solvent system comprising the mixture including the morpholine-based compound, such as N-formylmorpholine, and the alkoxybenzene-based compound.

As another example, the SPPS method can include the step of coupling in the presence of the solvent system comprising the mixture including the morpholine-based compound, such as N-formylmorpholine, and the alkoxybenzene-based compound.

As yet another example, the SPPS method can include the steps of coupling and washing, but not deprotecting, in the presence of the solvent system comprising the mixture including the morpholine-based compound, such as N-formylmorpholine, and the alkoxybenzene.

As yet another example, the SPPS method can include the steps of deprotecting, washing, and coupling in the presence of the solvent system comprising the mixture including the morpholine-based compound, such as N-formylmorpholine, and the alkoxybenzene-based compound.

The method can also use the solvent system including a mixture including the morpholine-based compound, such as N-formylmorpholine, and an alkoxy-based benzene compound described herein with polystyrene and/or PEG based resins.

In other examples, the SPPS method can include the step of deprotecting in the presence of the solvent system comprising the mixture including NBP and the alkoxybenzene-based compound.

As another example, the SPPS method can include the step of washing in the presence of the solvent system comprising the mixture including NBP and the alkoxybenzene-based compound.

As another example, the SPPS method can include the step of coupling in the presence of the solvent system comprising the mixture including NBP and the alkoxybenzene-based compound.

As yet another example, the SPPS method can include the steps of coupling and washing, but not deprotecting, in the presence of the solvent system comprising the mixture including NBP and the alkoxybenzene.

As yet another example, the SPPS method can include the steps of deprotecting, washing, and coupling in the presence of the solvent system comprising the mixture including NBP and the alkoxybenzene-based compound.

The method can also use the solvent system including a mixture including NBP and an alkoxy-based benzene compound described herein with polystyrene and/or PEG based resins.

Still further, in exemplary embodiments, the SPPS method can include the step of applying microwave energy during one or more of the SPPS steps, for example, during the deprotecting and/or coupling steps.

In exemplary embodiments, the SPPS method can further include the step of cleaving the peptide from the solid phase resin after the deprotecting, washing, and/or coupling steps. Methods and agents for cleaving a peptide from a solid phase resin are also well known in the art.

In exemplary embodiments, the method can use Fmoc solid phase peptide chemistry as known in the art.

In exemplary embodiments, the deprotection, washing, and/or coupling steps, for example, the deprotection and/or coupling steps, can be performed at elevated temperatures, for example at a temperature of about 30° C. or greater, for example about 30° C. to about 120° C., for example about 40° C. to about 120° C., for example about 70° C. to about 120° C., for example about 70° C. to about 110° C., for example about 90° C. to about 120° C., and for example about 90° C. to about 110° C., without limitation.

In exemplary embodiments, the SPPS method can optionally further include the step of diluting the SPPS solvent system described herein (including a morpholine-based compound, such as N-formylmorpholine, and an alkoxybenzene-based compound, and/or including NBP and an alkoxybenzene-based compound) by adding an additional solvent to the SPPS solvent system prior to and/or during the washing step. This can help improve SPPS efficiencies, for example, by reducing the total number of washing steps per cycle, decreasing the time required for each washing cycle, etc.

The diluting solvent can be selected, for example, to reduce viscosity of the SPPS solvent system. Examples of suitable additional diluting solvents include without limitation lower alkyl (C1-C4) alcohols, such as methanol, ethanol, 1-propanol, 2-propanol, n-butanol, isobutanol, and/or tert-butanol. Another exemplary additional diluting solvent is ethyl acetate.

The diluting step can include adding an additional solvent to the SPPS solvent system to provide a washing solvent system including the additional solvent in an amount greater than 0 wt % (i.e., some amount of additional diluting solvent is present) to about 90 wt %, for example about 50 wt % to about 85 wt %, and as another example about 80 wt %, based on the total weight (100 wt %) of the SPPS solvent system and the additional diluting solvent.

In exemplary embodiments, the diluted washing solvent system can include the SPPS solvent system (including a morpholine-based compound, such as N-formylmorpholine, and an alkoxybenzene-based compound, and/or including NBP and an alkoxybenzene-based compound) in an amount of less than about 100 wt % (some amount of the additional diluting solvent is present) to about 10 wt %, for example about 50 wt % to about 15 wt %, and as another example about 20 wt %, based on the total weight (100 wt %) of the SPPS solvent system and the additional diluting solvent.

In exemplary embodiments, the method can further include the step of preparing the solvent system, for example by combining the morpholine-based compound, such as N-formylmorpholine, and the alkoxybenzene-based compound, and/or by combining NBP and the alkoxybenzene-based compound, prior to and/or during any and/or all of deprotecting, coupling and/or washing steps (i.e., individually or in combination) of SPPS.

In exemplary embodiments, the method employs a solvent system as described herein comprising a mixture including a morpholine-based compound, such as N-formylmorpholine, and an alkoxybenzene-based compound, wherein the solvent mixture has a sufficiently high flash point for compliance with government regulations. In non-limiting examples of the method, the solvent mixture can have a flash point of about 93° C. or higher.

In exemplary embodiments, the SPPS method employs a solvent system as described herein comprising a mixture including a morpholine-based compound, such as N-formylmorpholine, and an alkoxybenzene-based compound, wherein the solvent mixture can include the morpholine-based compound, for example NFM, in an amount of about 20 wt % to about 50 wt %, for example, about 25 wt % to about 50 wt %, based on 100 wt % of the solvent mixture including the morpholine-based compound such as NFM and the alkoxybenzene-based compound. In some embodiments, the SPPS method employs a solvent mixture including the morpholine-based compound, for example NFM, in an amount of about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt % based on 100 wt % of the solvent mixture. Further, according to some embodiments, the morpholine-based compound, for example NFM, can be present in an amount of from about any of the foregoing amounts to about any other of the foregoing amounts.

In exemplary embodiments, the SPPS method employs a solvent system as described herein comprising a mixture including a morpholine-based compound, such as N-formylmorpholine, and an alkoxybenzene-based compound, wherein the solvent mixture can include the alkoxybenzene-based compound in an amount of about 50 wt % to about 80 wt %, for example, about 50 wt % to about 75 wt %, based on 100 wt % of the solvent mixture including the morpholine-based compound, for example NFM, and the alkoxybenzene-based compound. In some embodiments, the SPPS method employs the solvent mixture including the alkoxybenzene-based compound in an amount of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 wt % based on 100 wt % of the solvent mixture. Further, according to some embodiments, the alkoxybenzene-based compound can be present in an amount of from about any of the foregoing amounts to about any other of the foregoing amounts.

In exemplary embodiments, the SPPS method employs a solvent system as described herein comprising a mixture including NBP and an alkoxybenzene-based compound, wherein the solvent mixture can include NBP in an amount of about 20 wt % to about 50 wt %, for example, about 25 wt % to about 50 wt %, based on 100 wt % of the solvent mixture including NBP and the alkoxybenzene-based compound. In some embodiments, the SPPS method employs a solvent mixture including NBP in an amount of about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt % based on 100 wt % of the solvent mixture. Further, according to some embodiments, the NBP can be present in an amount of from about any of the foregoing amounts to about any other of the foregoing amounts.

In exemplary embodiments, the SPPS method employs a solvent system as described herein comprising a mixture including NBP and an alkoxybenzene-based compound, wherein the solvent mixture can include the alkoxybenzene-based compound in an amount of about 50 wt % to about 80 wt %, for example, about 50 wt % to about 75 wt %, based on 100 wt % of the solvent mixture including NBP and the alkoxybenzene-based compound. In some embodiments, the SPPS method employs the solvent mixture including the alkoxybenzene-based compound in an amount of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 wt % based on 100 wt % of the solvent mixture. Further, according to some embodiments, the alkoxybenzene-based compound can be present in an amount of from about any of the foregoing amounts to about any other of the foregoing amounts.

In exemplary embodiments of the SPPS method, the alkoxybenzene-based compound can include a compound of Formula 1:

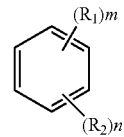

wherein:
each $R_1$ is independently —OR, wherein R is $C_1$-$C_4$ alkyl;
each $R_2$ is independently hydrogen or $C_1$-$C_4$ alkyl;
m is 1 or 2;
n is 4 or 5; and
m+n is 6.

Again, such alkoxybenzene-based compounds of Formula 1 are known in the art and are commercially available and/or can be produced by the skilled artisan without undue experimentation.

In exemplary embodiments of the SPPS method, the alkoxybenzene-based compound of Formula 1 can be a dialkoxybenzene-based compound, wherein m is 2. In such embodiments, each of the alkoxy substituents $R_1$ can be the same or different. For example, each $R_1$ can independently be methoxy, ethoxy, propoxy and/or butoxy, for example, each R can be methyl. Also when m is 2, in exemplary embodiments, each $R_2$ can be hydrogen. In alternative embodiments when m is 2, one or more, for example, one, two, three, or four $R_2$ can be $C_1$-$C_4$ alkyl, such as methyl, ethyl, propyl and/or butyl, and any remaining $R_2$ can be hydrogen.

In exemplary embodiments of the SPPS method, the dialkoxybenzene-based compound can include 1,3-dimethoxybenzene of the following formula:

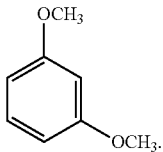

In exemplary embodiments of the SPPS method, the solvent mixture including NFM and 1,3-dimethoxybenzene can have a flash point of about 93° C. or higher.

In exemplary embodiments of the SPPS method, the solvent mixture can include about 20 wt % to about 50 wt % NFM and about 50 wt % to about 80 wt % 1,3-dimethoxybenzene, for example about 25 wt % to about 50 wt % NFM and about 50 wt % to about 75 wt % 1,3-dimethoxybenzene, and as another example about 25 wt % NFM and about 75 wt % 1,3-dimethoxybenzene, without being limited thereto.

In other exemplary embodiments of the SPPS method, the alkoxybenzene-based compound of Formula 1 can be an alkoxybenzene-based compound wherein m is 1. In such embodiments, the alkoxy substituent $R_1$ can be, for example, methoxy, ethoxy, propoxy or butoxy, for example R can be methyl. Also when m is 1, in exemplary embodiments, each $R_2$ can be hydrogen. In alternative embodiments when m is 1, one or more, for example, one, two, three, four, or five $R_2$ can be $C_1$-$C_4$ alkyl, such as methyl, ethyl, propyl and/or butyl, and any remaining $R_2$ can be hydrogen.

In exemplary embodiments of the SPPS method, the alkoxybenzene-based compounds can include anisole-based compounds. As a non-limiting example, the alkoxybenzene-based compound can be an anisole compound represented by the following Formula 2:

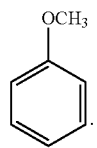

As another non-limiting example, the alkoxybenzene-based compound can be an anisole compound wherein one $R_2$ is $C_1$-$C_4$ alkyl, for example methyl, and the remaining $R_2$ are hydrogen, and wherein alkyl substituent $R_2$ is positioned ortho, meta, or para to the alkoxy substituent $R_1$. A non-limiting example of an alkyl-substituted anisole compound is represented by the following Formula 3:

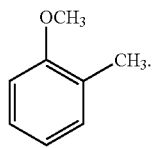

SPPS methods are well known in the art and can be readily conducted by the skilled artisan without undue experimentation.

The present disclosure also relates to a composition for solid phase peptide synthesis (SPPS), for example at elevated temperatures. The composition can include an amino acid linked to a solid phase resin; and a solvent system for solid phase peptide synthesis (SPPS) comprising a solvent mixture including a morpholine-based compound, for example N-formylmorpholine, and an alkoxybenzene-based compound, as described in more detail herein. In other embodiments. the composition can include an amino acid linked to a solid phase resin; and a solvent system for solid phase peptide synthesis (SPPS) comprising a solvent mixture including NBP and an alkoxybenzene-based compound, as described in more detail herein.

In other embodiments, the composition can include a solid phase resin for SPPS and a solvent system for solid phase peptide synthesis (SPPS) comprising a solvent mixture including a morpholine-based compound, for example N-formylmorpholine, and an alkoxybenzene-based compound, as described in more detail herein, and further optionally an amino acid. In other embodiments, the composition can include a solid phase resin for SPPS and a solvent system for solid phase peptide synthesis (SPPS) comprising a solvent mixture including NBP and an alkoxybenzene-based compound, as described in more detail herein, and further optionally an amino acid.

The composition for SPPS can further include an activator additive as known in the art.

In exemplary embodiments of the composition for SPPS, the amino acid is initially an Fmoc-protected amino acid also as known in the art.

In exemplary embodiments of the composition for SPPS, the solvent mixture including a morpholine-based compound, such as N-formylmorpholine, and an alkoxybenzene-based compound, can have a sufficiently high flash point for compliance with government regulations, for example, a flash point of about 93° C. or higher.

In exemplary embodiments of the composition for SPPS, the solvent mixture including a morpholine-based compound, such as N-formylmorpholine, and an alkoxybenzene-based compound can include the morpholine-based compound, for example NFM, in an amount of about 20 wt % to about 50 wt %, for example, about 25 wt % to about 50 wt %, based on 100 wt % of the solvent mixture including the morpholine-based compound such as NFM and the alkoxybenzene-based compound. In some embodiments, the composition for SPPS includes a solvent mixture including the morpholine-based compound, for example NFM, in an amount of about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt % based on 100 wt % of the solvent mixture. Further, according to some embodiments, the morpholine-based compound, for example NFM, can be present in an amount of from about any of the foregoing amounts to about any other of the foregoing amounts.

In exemplary embodiments of the composition for SPPS, the solvent mixture including a morpholine-based compound, such as N-formylmorpholine, and an alkoxybenzene-based compound can include the alkoxybenzene-based compound in an amount of about 50 wt % to about 80 wt %, for example, about 50 wt % to about 75 wt %, based on 100 wt % of the solvent mixture including the morpholine-based compound, for example NFM, and the alkoxybenzene-based compound. In some embodiments, the composition for SPPS includes a solvent mixture including the alkoxybenzene-based compound in an amount of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 wt % based on 100 wt % of the solvent mixture. Further, according to some embodiments, the alkoxybenzene-based compound can be present in an amount of from about any of the foregoing amounts to about any other of the foregoing amounts.

In exemplary embodiments of the composition for SPPS, the solvent mixture including NBP and an alkoxybenzene-based compound can include NBP in an amount of about 20 wt % to about 50 wt %, for example, about 25 wt % to about 50 wt %, based on 100 wt % of the solvent mixture including NBP and the alkoxybenzene-based compound. In some embodiments, the composition for SPPS includes a solvent mixture including NBP in an amount of about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt % based on 100 wt % of the solvent mixture. Further, according to some embodiments, NBP can be present in an amount of from about any of the foregoing amounts to about any other of the foregoing amounts.

In exemplary embodiments of the composition for SPPS, the solvent mixture including NBP and an alkoxybenzene-based compound can include the alkoxybenzene-based compound in an amount of about 50 wt % to about 80 wt %, for example, about 50 wt % to about 75 wt %, based on 100 wt % of the solvent mixture including NBP and the alkoxybenzene-based compound. In some embodiments, the composition for SPPS includes a solvent mixture including the alkoxybenzene-based compound in an amount of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 wt % based on 100 wt % of the solvent mixture. Further, according to some embodiments, the alkoxybenzene-based compound can be present in an amount of from about any of the foregoing amounts to about any other of the foregoing amounts.

In exemplary embodiments of the composition for SPPS, the alkoxybenzene-based compound can include a compound of Formula 1:

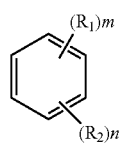

wherein:
each $R_1$ is independently —OR, wherein R is $C_1$-$C_4$ alkyl;
each $R_2$ is independently hydrogen or $C_1$-$C_4$ alkyl;
m is 1 or 2;
n is 4 or 5; and
m+n is 6.

Again, such alkoxybenzene-based compounds of Formula 1 are known in the art and are commercially available and/or can be produced by the skilled artisan without undue experimentation.

In exemplary embodiments of the composition for SPPS, the alkoxybenzene-based compound of Formula 1 can be a dialkoxybenzene-based compound, wherein m is 2. In such embodiments, each of the alkoxy substituents $R_1$ can be the same or different. For example, each $R_1$ can independently be methoxy, ethoxy, propoxy and/or butoxy, for example, each R can be methyl. Also when m is 2, in exemplary embodiments, each $R_2$ can be hydrogen. In alternative embodiments when m is 2, one or more, for example, one, two, three, or four $R_2$ can be $C_1$-$C_4$ alkyl, such as methyl, ethyl, propyl and/or butyl, and any remaining $R_2$ can be hydrogen.

In exemplary embodiments of the composition for SPPS, the dialkoxybenzene-based compound can include 1,3-dimethoxybenzene of the following formula:

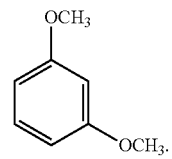

In exemplary embodiments of the composition for SPPS, the solvent mixture including NFM and 1,3-dimethoxybenzene can have a flash point of about 93° C. or higher.

In exemplary embodiments of the composition for SPPS, the solvent mixture can include about 20 wt % to about 50 wt % NFM and about 50 wt % to about 80 wt % 1,3-dimethoxybenzene, for example about 25 wt % to about 50 wt % NFM and about 50 wt % to about 75 wt % 1,3-dimethoxybenzene, and as another example about 25 wt % NFM and about 75 wt % 1,3-dimethoxybenzene, without being limited thereto.

In other exemplary embodiments of the composition for SPPS, the alkoxybenzene-based compound of Formula 1 can be an alkoxybenzene-based compound wherein m is 1. In such embodiments, the alkoxy substituent $R_1$ can be, for example, methoxy, ethoxy, propoxy or butoxy, for example R can be methyl. Also when m is 1, in exemplary embodiments, each $R_2$ can be hydrogen. In alternative embodiments when m is 1, one or more, for example, one, two, three, four, or five $R_2$ can be $C_1$-$C_4$ alkyl, such as methyl, ethyl, propyl and/or butyl, and any remaining $R_2$ can be hydrogen.

In exemplary embodiments of the composition for SPPS, the alkoxybenzene-based compounds can include anisole-based compounds. A non-limiting example of the alkoxybenzene-based compound is an anisole compound represented by the following Formula 2:

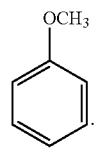

As another non-limiting example, the alkoxybenzene-based compound can be an anisole compound wherein one $R_2$ is $C_1$-$C_4$ alkyl, for example methyl, and the remaining $R_2$ are hydrogen, and wherein alkyl substituent $R_2$ is positioned ortho, meta, or para to the alkoxy substituent $R_1$. A non-limiting example of an alkyl-substituted anisole compound is represented by the following Formula 3:

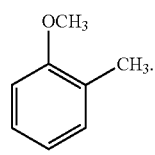

The present disclosure further relates to a composition including a peptide chain linked to a solid phase resin; and a solvent system for solid phase peptide synthesis (SPPS) comprising a solvent mixture including a morpholine-based compound, for example N-formylmorpholine, and an alkoxybenzene-based compound as described in more detail herein. The present disclosure further relates to a composition including a peptide chain linked to a solid phase resin; and a solvent system for solid phase peptide synthesis (SPPS) comprising a solvent mixture including NBP and an alkoxybenzene-based compound as described in more detail herein.

In exemplary embodiments of the composition including a peptide chain linked to a solid phase resin, the solvent mixture including a morpholine-based compound, such as N-formylmorpholine, and an alkoxybenzene-based compound, can have a sufficiently high flash point for compliance with government regulations, for example, a flash point of about 93° C. or higher.

In exemplary embodiments of the composition including a peptide chain linked to a solid phase resin, the solvent mixture including a morpholine-based compound, such as N-formylmorpholine, and an alkoxybenzene-based compound can include the morpholine-based compound, for example, NFM, in an amount of about 20 wt % to about 50 wt %, for example, about 25 wt % to about 50 wt %, based on 100 wt % of the solvent mixture including the morpholine-based compound such as NFM and the alkoxybenzene-based compound. In some embodiments, the composition includes a solvent mixture including the morpholine-based compound, for example NFM, in an amount of about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt % based on 100 wt % of the solvent mixture. Further, according to some embodiments, the morpholine-based compound, for example NFM, can be present in an amount of from about any of the foregoing amounts to about any other of the foregoing amounts.

In exemplary embodiments of the composition including a peptide chain linked to a solid phase resin, the solvent mixture including a morpholine-based compound, such as N-formylmorpholine, and an alkoxybenzene-based compound can include the alkoxybenzene-based compound in an amount of about 50 wt % to about 80 wt %, for example, about 50 wt % to about 75 wt %, based on 100 wt % of the solvent mixture including the morpholine-based compound, for example NFM, and the alkoxybenzene-based compound. In some embodiments, the composition includes a solvent mixture including the alkoxybenzene-based compound in an amount of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 wt % based on 100 wt % of the solvent mixture. Further, according to some embodiments, the alkoxybenzene-based compound can be present in an amount of from about any of the foregoing amounts to about any other of the foregoing amounts.

In exemplary embodiments of the composition including a peptide chain linked to a solid phase resin, the solvent mixture including NBP and an alkoxybenzene-based compound can include NBP in an amount of about 20 wt % to about 50 wt %, for example, about 25 wt % to about 50 wt %, based on 100 wt % of the solvent mixture including NBP and the alkoxybenzene-based compound. In some embodiments, the composition includes a solvent mixture including NBP in an amount of about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt % based on 100 wt % of the solvent mixture. Further, according to some embodiments, NBP can be present in an amount of from about any of the foregoing amounts to about any other of the foregoing amounts.

In exemplary embodiments of the composition including a peptide chain linked to a solid phase resin, the solvent mixture including NBP and an alkoxybenzene-based compound can include the alkoxybenzene-based compound in an amount of about 50 wt % to about 80 wt %, for example, about 50 wt % to about 75 wt %, based on 100 wt % of the solvent mixture including NBP and the alkoxybenzene-based compound. In some embodiments, the composition includes a solvent mixture including the alkoxybenzene-based compound in an amount of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 wt % based on 100 wt % of the solvent mixture. Further, according to some embodiments, the alkoxybenzene-based compound can be present in an amount of from about any of the foregoing amounts to about any other of the foregoing amounts.

In exemplary embodiments of the composition including a peptide chain linked to a solid phase resin, the alkoxybenzene-based compound can include a compound of Formula 1:

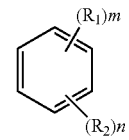

wherein:
each $R_1$ is independently —OR, wherein R is $C_1$-$C_4$ alkyl;
each $R_2$ is independently hydrogen or $C_1$-$C_4$ alkyl;
m is 1 or 2;
n is 4 or 5; and
m+n is 6.

Again, such alkoxybenzene-based compounds of Formula 1 are known in the art and are commercially available and/or can be produced by the skilled artisan without undue experimentation.

In exemplary embodiments of the composition including a peptide chain linked to a solid phase resin, the alkoxybenzene-based compound of Formula 1 can be a dialkoxybenzene-based compound, wherein m is 2. In such embodiments, each of the alkoxy substituents $R_1$ can be the same or different. For example, each $R_1$ can independently be methoxy, ethoxy, propoxy and/or butoxy, for example, each R can be methyl. Also when m is 2, in exemplary embodiments, each $R_2$ can be hydrogen. In alternative embodiments when m is 2, one or more, for example, one, two, three, or four $R_2$ can be $C_1$-$C_4$ alkyl, such as methyl, ethyl, propyl and/or butyl, and any remaining $R_2$ can be hydrogen.

In exemplary embodiments of the composition including a peptide chain linked to a solid phase resin, the dialkoxybenzene-based compound can include 1,3-dimethoxybenzene of the following formula:

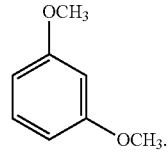

In exemplary embodiments of the composition including a peptide chain linked to a solid phase resin, the solvent mixture including NFM and 1,3-dimethoxybenzene can have a flash point of about 93° C. or higher.

In exemplary embodiments of the composition including a peptide chain linked to a solid phase resin, the solvent mixture can include about 20 wt % to about 50 wt % NFM and about 50 wt % to about 80 wt % 1,3-dimethoxybenzene, for example about 25 wt % to about 50 wt % NFM and about 50 wt % to about 75 wt % 1,3-dimethoxybenzene, and as another example about 25 wt % NFM and about 75 wt % 1,3-dimethoxybenzene, without being limited thereto.

In other exemplary embodiments of the composition including a peptide chain linked to a solid phase resin, the alkoxybenzene-based compound of Formula 1 can be an alkoxybenzene-based compound wherein m is 1. In such embodiments, the alkoxy substituent $R_1$ can be, for example, methoxy, ethoxy, propoxy or butoxy, for example R can be methyl. Also when m is 1, in exemplary embodiments, each $R_2$ can be hydrogen. In alternative embodiments when m is 1, one or more, for example, one, two, three, four, or five $R_2$ can be $C_1$-$C_4$ alkyl, such as methyl, ethyl, propyl and/or butyl, and any remaining $R_2$ can be hydrogen.

In exemplary embodiments of the composition including a peptide chain linked to a solid phase resin, the alkoxybenzene-based compound can include an anisole-based compound. A non-limiting example of the alkoxybenzene-based compound is an anisole compound represented by the following Formula 2:

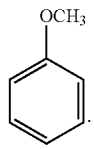

As another non-limiting example, the alkoxybenzene-based compound can be an anisole compound wherein one $R_2$ is C1-C4 alkyl, for example methyl, and the remaining $R_2$ are hydrogen, and wherein alkyl substituent $R_2$ is positioned ortho, meta, or para to the alkoxy substituent $R_1$. A non-limiting example of an alkyl-substituted anisole compound is represented by the following Formula 3:

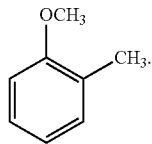

Without being bound by any explanation or theory, in an effort to develop a total replacement for the undesirable dipolar aprotic solvents (DMF, DMA, and NMP) currently in use for SPPS the inventors investigated creating a unique solvent combination. It was felt that incorporating a formyl group that is contained within DMF would be ideal for minimizing peptide aggregation due to its similarity to an amide bond. Surveying the known formyl solvents, N-formylmorpholine is unique in its low toxicity. However, it suffers from challenges related to its high melting point, low viscosity, limited swelling of non-polar groups, and observed low swelling of polystyrene resin.

The inventors therefore felt that finding a solvent that could work in combination with NFM to overcome these difficulties might offer an ideal solution. Solvents that contained an ester group were seen as not-ideal due to their lower stability particularly at elevated temperature. Solvents that contain a phenyl group were then investigated due to their potential ability to solvate non-polar protecting groups such as Trityl and also improve swelling of polystyrene resins that contain phenyl groups. Many solvents within this class have undesirable toxicity and safety properties such as benzene, toluene, and xylenes. However, anisole is ranked as a preferred solvent and appears unreactive. It also contains an advantageously higher boiling point (≥150 C) that is useful for SPPS at elevated temperature. Pleasingly, a 25-35% mixture of NFM and Anisole showed a significant improvement in solvation of all 20 Fmoc amino acids (≥0.2M). The viscosity of the combined solution also appeared much less than NFM alone and suitable for use in automated processes.

The inventors further investigated the use of various mixed solvent systems as a general replacement for DMF through the synthesis of a variety of difficult peptides using both polystyrene and PEG based resins (ProTide) with Fmoc chemistry.

For example, DMF is compared to the following mixed solvent systems in the synthesis of [65-74]ACP: 35 wt % NFM and anisole; 25 wt % NFM and 1,2-dimethoxybenzene (1,2-DMB); and 25 wt % NFM and 1,3-dimethoxybenzene (1,3-DMB). As indicated in Table 1 below, the 35% NFM in anisole mixture and the 25 wt % NFM in 1,3-DMB mixture as the solvent for all reagents and washing result in similar crude purity as compared to using DMF for all reagents and washing.

TABLE 1

Synthesis of [65-74] ACP with Different Solvents

| Entry | Resin | Deprotection Solvent | Washing Solvent | Coupling Solvent | % Purity (UPLC-MS) |
|---|---|---|---|---|---|
| 1 | Rink Amide ProTide | DMF | DMF | DMF | 91 |
| 2 | Rink Amide ProTide | 35% NFM/Anisole | 35% NFM/Anisole | 35% NFM/Anisole | 87 |
| 3 | Rink Amide MBHA PS | 25% NFM/1,2-DMB | 25% NFM/1,2-DMB | 25% NFM/1,2-DMB | 72 |
| 4 | Rink Amide MBHA PS | 25% NFM/1,3-DMB | 25% NFM/1,3-DMB | 25% NFM/1,3-DMB | 90 |

Experiment Conditions for Entries 1-3

Peptide Sequence ($^{65-74}$ACP)=(SEQ ID NO: 1) VQAAIDYING-NH2
Synthesis Scale=0.1 mmol
Instrument=Liberty Blue Microwave Peptide Synthesizer (CEM Corp., Matthews, N.C.)
Deprotection=20% piperidine
Microwave Deprotection Method=1 min at 100° C.
Washing=Post-Deprotection (2 mL, 2 mL, 3 mL); Post-Coupling=None
Coupling=5-fold excess of AA/DIC/Oxyma (1:2.1) in 4 mL solution
Microwave Coupling Method=2 min at 100° C.
Cleavage=5 mL of TFA/TIS/H$_2$O/DODt (92.5:2.5:2.5:2.5) for 30 min at 38° C. in a RAZOR cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)

Experiment Conditions for Entry 4

Peptide Sequence ($^{65-74}$ACP)=(SEQ ID NO: 1) VQAAIDYING-NH$_2$
Synthesis Scale=0.1 mmol
Instrument=Liberty PRIME Microwave Peptide Synthesizer (CEM Corp., Matthews, N.C.)
Deprotection=75% pyrrolidine
Microwave Deprotection Method=60 sec at 110° C.
Washing=Post-Deprotection (3×4 mL); Post-Coupling=None
Coupling=5-fold excess of AA/DIC/Oxyma (1:2.1) in 4 mL solution
Microwave Coupling Method=30 sec wait-90 sec at 105° C.
Cleavage=5 mL of TFA/TIS/H$_2$O/DODt (92.5:2.5:2.5:2.5) for 30 min at 38° C. in a RAZOR cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)
DMF is also compared to a mixed solvent system including 25 wt % NFM and 1,3-dimethoxybenzene (1,3-DMB) in the synthesis of JR 10 mer. As indicated in Table 2 below, the 25 wt % NFM in 1,3-DMB mixture as the solvent for all reagents and washing results in improved crude purity as compared to using DMF for all reagents and washing.

Experiment Conditions for Entry 1

Peptide Sequence (JR 10 mer)=(SEQ ID NO: 2) WFTTLISTM-NH$_2$
Synthesis Scale=0.1 mmol
Instrument=Liberty PRIME Microwave Peptide Synthesizer (CEM Corp., Matthews, N.C.)
Deprotection=25% pyrrolidine
Microwave Deprotection Method=40 sec at 110° C.
Washing=Post-Deprotection (2×4 mL); Post-Coupling=None
Coupling=5-fold excess of AA/DIC/Oxyma (1:2.1) in 3.5 mL solution
Microwave Coupling Method=30 sec wait-60 sec at 105° C.
Cleavage=5 mL of TFA/TIS/H$_2$O/DODt (92.5:2.5:2.5:2.5) for 30 min at 38° C. in a RAZOR cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm

Experiment Conditions for Entry 2:

Peptide Sequence (JR 10 mer)=(SEQ ID NO: 2) WFTTLISTM-NH$_2$
Synthesis Scale=0.1 mmol
Instrument=Liberty PRIME Microwave Peptide Synthesizer (CEM Corp., Matthews, N.C.)
Deprotection=75% pyrrolidine
Microwave Deprotection Method=60 sec at 110° C.
Washing=Post-Deprotection (3×4 mL); Post-Coupling=None
Coupling=5-fold excess of AA/DIC/Oxyma (1:2.1) in 4 mL solution
Microwave Coupling Method=30 sec wait-90 sec at 105° C.
Cleavage=5 mL of TFA/TIS/H$_2$O/DODt (92.5:2.5:2.5:2.5) for 30 min at 38° C. in a RAZOR cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)
DMF is also compared to the following mixed solvent systems in the synthesis of the more difficult Thymosin sequence as shown in Table 3: 25 wt % NFM and anisole; and 25 wt % NFM and 1,3-dimethoxybenzene (1,3-DMB). As indicated in Table 3 below, the 25% NFM in anisole mixture and the 25 wt % NFM in 1,3-DMB mixture as the solvent for all reagents and washing result in similar and/or improved crude purity as compared to using DMF for all reagents and washing.

TABLE 2

Synthesis of JR 10 mer with Different Solvents

| Entry | Resin | Deprotection Solvent | Washing Solvent | Coupling Solvent | % Purity (UPLC-MS) |
|---|---|---|---|---|---|
| 1 | Rink Amide ProTide | DMF | DMF | DMF | 70% |
| 2 | Rink Amide ProTide | 25% NFM/1,3-DMB | 25% NFM/1,3-DMB | 25% NFM/1,3-DMB | 76% |

TABLE 3

Synthesis of Thymosin with Different Solvents

| Entry | Resin | Deprotection Solvent | Washing Solvent | Coupling Solvent | % Purity (UPLC-MS) |
|---|---|---|---|---|---|
| 1 | Rink Amide MBHA PS | DMF | DMF | DMF | 73 |
| 2 | Rink Amide MBHA PS | 25% NFM/Anisole | 25% NFM/Anisole | 25% NFM/Anisole | 77 |
| 3 | Rink Amide ProTide | DMF | DMF | DMF | 76 |
| 4 | Rink Amide ProTide | 25% NFM/Anisole | 25% NFM/Anisole | 25% NFM/Anisole | 79 |
| 5 | Rink Amide ProTide | 25% NFM/1,3-DMB | 25% NFM/1,3-DMB | 25% NFM/1,3-DMB | 75 |

Experiment Conditions for Entry 1-4

Peptide Sequence (Thymosin)=(SEQ ID NO: 3)

SDAAVDTSSEITTKDLKEKKEVVEEAEN-NH$_2$

Synthesis Scale=0.1 mmol
Instrument=Liberty Blue Microwave Peptide Synthesizer (CEM Corp., Matthews, N.C.)
Deprotection=20% piperidine
Microwave Deprotection Method=1 min at 100° C.
Washing=Post-Deprotection (2 mL, 2 mL, 3 mL); Post-Coupling=None
Coupling=5-fold excess of AA/DIC/Oxyma (1:2.1) in 4 mL solution
Microwave Coupling Method=2 min at 100° C.
Cleavage=5 mL of TFA/TIS/H$_2$O/DODt (92.5:2.5:2.5:2.5) for 30 min at 38° C. in a RAZOR cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)

Experiment Conditions for Entry 5

Peptide Sequence (Thymosin)=(SEQ ID NO: 3)

SDAAVDTSSEITTKDLKEKKEVVEEAEN-NH$_2$

Synthesis Scale=0.1 mmol
Instrument=Liberty PRIME Microwave Peptide Synthesizer (CEM Corp., Matthews, N.C.)
Deprotection=75% pyrrolidine
Microwave Deprotection Method=60 sec at 110° C.
Washing=Post-Deprotection (3×4 mL); Post-Coupling=None
Coupling=5-fold excess of AA/DIC/Oxyma (1:2.1) in 4 mL solution
Microwave Coupling Method=30 sec wait-90 sec at 105° C.
Cleavage=5 mL of TFA/TIS/H$_2$O/DODt (92.5:2.5:2.5:2.5) for 30 min at 38° C. in a RAZOR cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)

DMF is also compared to the following mixed solvent systems in the synthesis of the ABC-20 mer peptide that encompasses all 20 of the standard amino acids with a PEG (ProTide) resin as shown in Table 4: 25 wt % NFM and anisole; and 25 wt % NFM and 1,3-dimethoxybenzene (1,3-DMB). As indicated in Table 4 below, the 25% NFM in anisole mixture and the 25 wt % NFM in 1,3-DMB mixture as the solvent for all reagents and washing result in similar crude purity as compared to using DMF for all reagents and washing.

TABLE 4

Synthesis of ABC-20 mer with Different Solvents

| Entry | Resin | Deprotection Solvent | Washing Solvent | Coupling Solvent | % Purity (UPLC-MS) |
|---|---|---|---|---|---|
| 1 | Rink Amide ProTide | DMF | DMF | DMF | 87 |
| 2 | Rink Amide ProTide | 25% NFM/Anisole | 25% NFM/Anisole | 25% NFM/Anisole | 86 |
| 3 | Rink Amide ProTide | 25% NFM/1,3-DMB | 25% NFM/1,3-DMB | 25% NFM/1,3-DMB | 77 |

Experiment Conditions for Entry 1-2

Peptide Sequence (ABC-20 mer)=(SEQ ID NO: 4)

VYWTSPFMKLIHEQCNRADG-NH$_2$

Synthesis Scale=0.1 mmol
Instrument=Liberty Blue Microwave Peptide Synthesizer (CEM Corp., Matthews, N.C.)
Deprotection=20% piperidine
Microwave Deprotection Method=1 min at 90° C.
Washing=Post-Deprotection (2 mL, 2 mL, 3 mL); Post-Coupling=None
Coupling=5-fold excess of AA/DIC/Oxyma (1:2.1) in 4 mL solution Microwave Coupling Method=2 min at 90° C.

Cleavage=5 mL of TFA/TIS/H₂O/DODt (92.5:2.5:2.5:2.5) for 30 min at 38° C. in a RAZOR cleavage system (CEM Corp., Matthews, N.C.)

Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)

Experiment Conditions for Entry 3

Peptide Sequence (ABC-20 mer)=(SEQ ID NO: 4)

VYWTSPFMKLIHEQCNRADG-NH₂

Synthesis Scale=0.1 mmol
Instrument=Liberty PRIME Microwave Peptide Synthesizer (CEM Corp., Matthews, N.C.)
Deprotection=75% pyrrolidine
Microwave Deprotection Method=60 sec at 110° C.
Washing=Post-Deprotection (3×4 mL); Post-Coupling=None
Coupling=5-fold excess of AA/DIC/Oxyma (1:2.1) in 4 mL solution
Microwave Coupling Method=30 sec wait-90 sec at 105° C.

Cleavage=5 mL of TFA/TIS/H₂O/DODt (92.5:2.5:2.5:2.5) for 30 min at 38° C. in a RAZOR cleavage system (CEM Corp., Matthews, N.C.)

Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)

The ABC 20mer is a good sequence for comparing epimerization as it encompasses all 20 natural amino acids and a c-terminal placed Asp-Gly segment which can epimerize as a by-product of aspartimide formation. Analysis of the ABC 20 per peptide synthesized in the new NFM/Anisole solvent mixture showed in general a lower level of epimization than when synthesized in DMF. This is significant in that the solvent mixture appears to be at least as good as DMF for minimizing this difficult to control side reaction.

| | CAT Results |
|---|---|
| ABC 20 mer with DMF | ABC 20 mer with NFM/Anisole (25/75) |
| Double DIC method: | Double DIC method: |
| 1 min/90 C. deprotection | 1 min/90 C. deprotection |
| 2 min/90 C. coupling | 2 min/90 C. coupling |
| AA/DIC/Oxyma (5/10/5) | AA/DIC/Oxyma (5/10/5) |
| 0.2M AA = 2.5 mL | 0.2M AA = 2.5 mL |
| M DIC = 1.0 mL | M DIC = 1.0 mL |
| 1.0M Oxyma = 0.5 mL | 1.0M Oxyma = 0.5 mL |
| Use Fmoc-His(Boc)-OH and Fmoc Asp(OMpe)-OH | Use Fmoc-His(Boc)-OH and Fmoc-Asp(OMpe)-OH |
| All others standard amino acids. Double Arg coupling. | All others standard amino acids,.Double Arg coupling. |
| Crude purity- | Crude purity- |
| 87% Alanine | 86% Alanine |
| 0.31% D-Enantiomer Valine | 0.15% D-Enantiomer Valine |
| <0.10% D-Enantiomer Threonine | <0.10% D-Enantiomer Threonine |
| >99.7% L-Threonine | >99.7% L-Threonine |
| <0.10% D-Threonine | <0.10% D-Threonine |
| <0.10% L-allo Threonine | <0.10% L-allo Threonine |
| <0.10% D-allo Threonine Isoleucine | <0.10% D-allo Threonine Isoleucine |
| >99.7% L-Isoleucine | >99.7% L-Isoleucine |
| <0.10% D-Isoleucine | <0.10% D-Isoleucine |
| <0.10% L-allo-Isoleucine | <0.10% L-allo-Isoleucine |
| <0.10% D-allo-Isoleucine Proline | <0.10% D-allo-Isoleucine Proline |
| 0.11% D-Enantiomer Leucine | <0.10% D-Enantiomer Leucine |
| 0.12% D-Enantiomer Serine | 0.14% D-Enantiomer Serine |
| 0.14% D-Enantiomer Cysteine | 0.11% D-Enantiomer Cysteine |
| 0.64% D-Enantiomer Aspartic acid | 0.95% D-Enantiomer Aspartic acid |
| 1.42% D-Enantiomer Methionine | 0.45% D-Enantiomer Methionine |
| 0.30% D-Enantiomer Phenylalanine | 0.14% D-Enantiomer Phenylalanine |
| 0.14% D-Enantiomer Glutamic acid | 0.19% D-Enantiomer Glutamic acid |
| 1.22% D-Enantiomer Tyrosine | 1.08% D-Enantiomer Tyrosine |
| 0.15% D-Enantiomer Lysine | 0.11% D-Enantiomer Lysine |
| 0.10% D-Enantiomer Arginine | <0.10% D-Enantiomer Arginine |
| 0.13% D-Enantiomer Tryptophan | 0.28% D-Enantiomer Tryptophan |
| 0.14% D-Enantiomer Histidine | <0.10% D-Enantiomer Histidine |
| 1.12% D-Enantiomer | 0.64% D-Enantiomer |

It is within the scope of this disclosure for one or more of the terms "substantially," "about," "approximately," and/or the like, to qualify each adjective and adverbs of the foregoing disclosure, to provide a broad disclosure. As an example, it is believed those of ordinary skill in the art will readily understand that, in different implementations of the features of this disclosure, reasonably different engineering tolerances, precision, and/or accuracy may be applicable and suitable for obtaining the desired result. Accordingly, it is believed those of ordinary skill will readily understand usage herein of the terms such as "substantially," "about," "approximately," and the like.

The use of the term "and/or" includes any and all combinations of one or more of the associated listed items.

In the foregoing, examples of embodiments have been disclosed. The present invention is not limited to such exemplary embodiments. In the foregoing, descriptions of sequences of steps or other actions are described for purposes of providing examples, and not for the purpose of limiting the scope of this disclosure (e.g., where appropriate: steps or actions may be performed in different sequences than described above, and steps and actions may be omitted and/or added). Unless otherwise noted, specific terms have been used in a generic and descriptive sense and not for purposes of limitation.

That which is claimed is:

1. A solid phase peptide synthesis (SPPS) solvent system comprising a solvent mixture including N-formylmorpholine and an alkoxybenzene-based compound, wherein the solvent mixture has a boiling point of about 140° C. or greater suitable for use with elevated SPPS temperatures.

2. The solvent system of claim 1, comprising about 20 wt % to about 50 wt % N-formylmorpholine and about 50 wt % to about 80 wt % of the alkoxybenzene-based compound.

3. The solvent system of claim 1, wherein the solvent mixture has a flash point of about 93° C. or higher.

4. The solvent system of claim 1, wherein the alkoxybenzene-based compound comprises a compound of Formula 1:

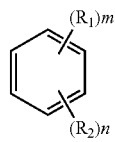

wherein:
each $R_1$ is independently —OR, wherein R is $C_1$-$C_4$ alkyl;
each $R_2$ is independently hydrogen or $C_1$-$C_4$ alkyl;
m is 1 or 2;
n is 4 or 5; and
m+n is 6.

5. The solvent system of claim 4, wherein m is 2.

6. The solvent system of claim 5, wherein each R is methyl.

7. The solvent system of claim 5, wherein each $R_2$ is hydrogen.

8. The solvent system of claim 5, wherein one or more of $R_2$ is $C_1$-$C_4$ alkyl.

9. The solvent system of claim 5, wherein the alkoxybenzene-based compound is 1,3-dimethoxybenzene:

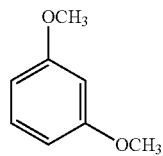

and wherein the solvent mixture has a flash point of about 93° C. or higher.

10. The solvent system of claim 9, comprising about 20 wt % to about 50 wt % N-formylmorpholine and about 50 wt % to about 80 wt % 1,3-dimethoxybenzene.

11. The solvent system of claim 9, comprising about 25 wt % to about 50 wt % N-formylmorpholine and about 50 wt % to about 75 wt % 1,3-dimethoxybenzene.

12. The solvent system of claim 4, wherein m is 1.

13. The solvent system of claim 12, wherein R is methyl.

14. The solvent system of claim 12, wherein each $R_2$ is H.

15. The solvent system of claim 12, wherein one or more of $R_2$ is $C_1$-$C_4$ alkyl.

16. The solvent system of claim 12, wherein one $R_2$ is $C_1$-$C_4$ alkyl and the remaining $R_2$ are hydrogen.

17. The solvent system of claim 16, wherein one $R_2$ is methyl and the remaining $R_2$ are hydrogen.

18. The solvent system of claim 12, wherein the alkoxybenzene-based compound is an anisole compound of Formula 2:

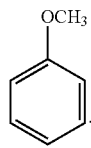

19. The solvent system of claim 12, wherein the alkoxybenzene-based compound is an anisole compound of Formula 3:

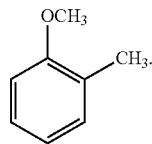

20. The solvent system of claim 1, wherein the solvent mixture has a boiling point suitable for use at a SPPS reaction temperature of about 70° C. to about 110° C.

21. The solvent system of claim 1, wherein N-formylmorpholine and the alkoxybenzene-based compound each have a boiling point of about 140° C. or greater.

22. The solvent system of claim 1, wherein the solvent mixture has a viscosity suitable for SPPS and is compatible with polystyrene and/or PEG resins.

23. The solvent system of claim 1, wherein the solvent mixture produces purity yields comparable to conventional solvents selected from the group consisting of DMF, DMA, and NMP.

24. The solvent system of claim 1, wherein the solvent mixture dissolves Fmoc amino acids at concentrations ≥0.2M.

25. A solvent system for solid phase peptide synthesis (SPPS) comprising a solvent mixture of N-formylmorpholine and a dialkoxybenzene compound of Formula 1a:

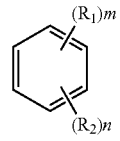

wherein:
each $R_1$ is independently —OR, wherein R is $C_1$-$C_4$ alkyl;
each $R_2$ is independently hydrogen or $C_1$-$C_4$ alkyl;
m is 2; and
n is 4,
wherein the solvent mixture has a boiling point of about 140° C. or greater suitable for use with elevated SPPS temperatures.

26. The solvent system of claim 25, wherein the dialkoxybenzene compound of Formula 1a is 1,3-dimethoxybenzene, the solvent system comprises about 20 wt % to about 50 wt % N-formylmorpholine and about 50 wt % to about 80 wt % 1,3-dimethoxybenzene, and the solvent mixture has a flash point of about 93° C. or higher.

27. A solvent system for solid phase peptide synthesis (SPPS) comprising a solvent mixture including N-formylmorpholine and an alkoxybenzene compound of Formula 1b:

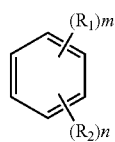

wherein:
$R_1$ is —OR, wherein R is $C_1$-$C_4$ alkyl;
each $R_2$ is independently hydrogen or $C_1$-$C_4$ alkyl;
m is 1; and
n is 5,
wherein the solvent mixture has a boiling point of about 140° C. or greater suitable for use with elevated SPPS temperatures.

28. The solvent system of claim 27, wherein the alkoxybenzene compound is a compound of Formula 2:

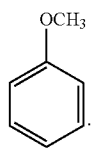

29. A solid phase peptide synthesis (SPPS) solvent system comprising a solvent mixture including N-butylpyrrolidinone (NBP) and an alkoxybenzene-based compound, wherein the solvent mixture has a boiling point of about 140'T or greater suitable for use with elevated SPPS temperatures.

30. The solvent system of claim 29, wherein the alkoxybenzene-based compound comprises a compound of Formula 1:

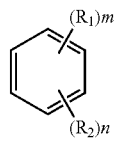

wherein:
each $R_1$ is independently —OR, wherein R is $C_1$-$C_4$ alkyl;
each $R_2$ is independently hydrogen or $C_1$-$C_4$ alkyl;
m is 1 or 2;
n is 4 or 5; and
m+n is 6.

31. A solid phase peptide synthesis (SPPS) method comprising the steps of:
deprotecting a first amino acid linked to a solid phase resin by removing a protective chemical group to form a deprotected amino acid;
washing the deprotected amino acid;
coupling a second amino acid to the deprotected amino acid to form a peptide from the first and second amino acids; and
repeating the deprotecting, washing, and coupling steps to form a peptide comprising the first, second, and successive amino acids,
wherein the deprotecting, washing, and/or coupling steps are performed in the presence of a solvent system comprising a solvent mixture including N-formylmorpholine and an alkoxybenzene-based compound,
wherein the solvent mixture has a boiling point of about 140° C. or greater suitable for use with elevated SPPS temperatures.

32. The SPPS method of claim 31, further comprising applying microwave energy during the deprotecting and/or coupling steps.

33. The SPPS method of claim 31, comprising conducting the deprotecting and/or coupling steps at a temperature of about 30° C. to about 120° C.

34. The SPPS method of claim 31, comprising conducting the deprotecting and/or coupling steps at a temperature of about 70° C. to about 110° C.

35. The SPPS method of claim 31, wherein the solvent system comprises about 20 wt % to about 50 wt % N-formylmorpholine and about 50 wt % to about 80 wt % of the alkoxybenzene-based compound.

36. The SPPS method of claim 31, wherein the alkoxybenzene-based compound comprises a compound of Formula 1:

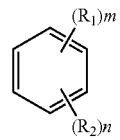

wherein:
each $R_1$ is independently —OR, wherein R is $C_1$-$C_4$ alkyl;
each $R_2$ is independently hydrogen or $C_1$-$C_4$ alkyl;
m is 1 or 2;
n is 4 or 5; and
m+n is 6.

37. The SPPS method of claim 31, wherein the alkoxybenzene-based compound is 1,3-dimethoxybenzene:

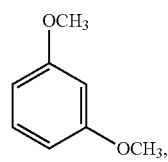

wherein the solvent mixture has a flash point of about 93° C. or higher.

38. The SPPS method of claim 31, wherein the alkoxybenzene-based compound is an anisole compound of Formula 2:

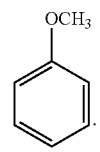

39. The solvent system of claim 29, comprising about 20 wt % to about 50 wt % N-butylpyrrolidinone and about 50 wt % to about 80 wt % of the alkoxybenzene-based compound.

40. The solvent system of claim 29, wherein the solvent mixture has a boiling point suitable for use at a SPPS reaction temperature of about 70° C. to about 110° C.

41. The solvent system of claim 29, wherein N-butylpyrrolidinone and the alkoxybenzene-based compound each have a boiling point of about 140° C. or greater.

42. The solvent system of claim 30, wherein m is 2.

43. The solvent system of claim 42, wherein the alkoxybenzene-based compound is 1,3-dimethoxybenzene:

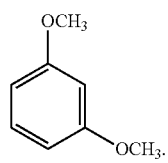

44. The solvent system of claim 30, wherein m is 1.

45. The solvent system of claim 44, wherein the alkoxybenzene-based compound is an anisole compound of Formula 2:

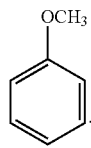

46. The solvent system of claim 44, wherein R is methyl.

47. The solvent system of claim 44, wherein each $R_2$ is H.

48. The solvent system of claim 44, wherein one or more of $R_2$ is $C_1$-$C_4$ alkyl.

49. The solvent system of claim 44, wherein one $R_2$ is $C_1$-$C_4$ alkyl and the remaining $R_2$ are hydrogen.

50. The solvent system of claim 49, wherein one $R_2$ is methyl and the remaining $R_2$ are hydrogen.

51. The solvent system of claim 44, wherein the alkoxybenzene-based compound is an anisole compound of Formula 3:

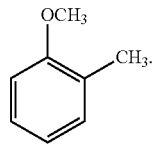

* * * * *